United States Patent

Nogami et al.

[11] Patent Number: 5,618,646
[45] Date of Patent: Apr. 8, 1997

[54] ELECTROPHOTOGRAPHIC PHOTORECEPTORS WITH ANTI-OXIDIZING AGENTS

[75] Inventors: Sumitaka Nogami; Michihiro Kitazawa; Katsuhiro Sato; Yoshimasa Tomiuchi, all of Kawasaki, Japan

[73] Assignee: Fuji Electric Co., Ltd., Kanagawa, Japan

[21] Appl. No.: 586,467

[22] Filed: Jan. 11, 1996

[30] Foreign Application Priority Data

Jan. 10, 1995 [JP] Japan ................................. 7-001615
Feb. 17, 1995 [JP] Japan ................................. 7-029050

[51] Int. Cl.$^6$ .............................................. G03G 5/047
[52] U.S. Cl. ........................... 430/59; 430/58; 430/64; 430/83
[58] Field of Search .......................... 430/58, 59, 83

[56] References Cited

U.S. PATENT DOCUMENTS

| 5,171,651 | 12/1992 | Takaoka et al. ................. 430/58 |
| 5,286,588 | 2/1994 | Suzuki ............................. 430/58 |
| 5,294,510 | 3/1994 | Ueda et al. ...................... 430/58 |
| 5,308,727 | 5/1994 | Osawa et al. .................... 430/58 |
| 5,324,610 | 6/1994 | Tanaka et al. ................... 430/58 |
| 5,380,613 | 1/1995 | Ueda et al. ...................... 430/59 X |
| 5,474,868 | 12/1995 | Adachi et al. ................... 430/59 X |

FOREIGN PATENT DOCUMENTS

| 187013 | 7/1986 | European Pat. Off. . |
| 2421536 | 11/1974 | Germany . |
| 3638418 | 5/1987 | Germany . |
| 4406244 | 9/1994 | Germany . |
| 297957 | 4/1990 | Japan . |
| 2201255 | 8/1988 | United Kingdom . |

*Primary Examiner*—Roland Martin
*Attorney, Agent, or Firm*—Spencer & Frank

[57] ABSTRACT

An electrophotographic photoreceptor has a conductive substrate and a photosensitive layer formed on the substrate. The photosensitive layer contains one compound which is selected from the group of the compounds represented by the formulae (I), (II), (III), (IV), and (V). Therefore, the electrophotographic photoreceptor shows stable characteristics, good durability, and long span of life in repeat use.

12 Claims, 1 Drawing Sheet

ELECTROPHOTOGRAPHIC PHOTORECEPTORS WITH ANTI-OXIDIZING AGENTS

BACKGROUND OF THE INVENTION

1. Field of the Invention

The present invention relates to an electrophotographic photoreceptor comprising a conductive substrate on which a photosensitive layer containing a pigment as a photoconductive material, a binder resin, an organic charge-transport agent, and the like is formed.

2. Description of the Prior Art

Conventionally, it has been well known that inorganic materials such as cadmium sulfide and zinc oxide and organic materials such as polyvinyl carbazole are provided as photoconductive materials to be included in photosensitive layers of electrophotographic photoreceptors. In addition, single-layer type photoreceptors have been also known. In this case, a photosensitive layer of each of them is formed as a single film including at least one of the above photosensitive materials.

In recent years, in addition, functionally distinguishable type photoreceptors have been developed as the high sensitive photoreceptors and they have been provided in practical use. In the functionally distinguishable type photoreceptor, the photoconductive functions thereof are divided into two different layers. That is, a charge generation layer for generating charge-carriers by the absorption of exposure and a charge transport layer for holding the electrical potential in dark and transporting the charge carriers.

Furthermore, the photoreceptors using organic materials as main components in their photosensitive layers, especially for their charge transport layers provided as the greater parts thereof, have been studied by many researchers and partially put into practical use by virtue of their advantage features of flexibility and excellent charging abilities, as the characteristics of the organic materials. In addition, they show excellent membrane-formabilities and cost effectiveness in their manufacturing processes.

For obtaining a reproduced image or the like, by the way, an electrophotographic device repeats the cycle of the steps of charging, image exposure, development, transferring, cleaning, and the like to the photoreceptor provided as a constituent part of the device. During the period of repeating the above cycle, the characteristics of the photoreceptor should be kept in stable. In the case of the above photoreceptor using the organic material as one of its main components, especially the functionally distinguishable type photoreceptor comprising a charge transport layer using an organic charge generation material has the excellent properties of charging, photo-sensitivities, and so on. However, these advantages are not enough to satisfy all of the requirements for the photoreceptor. That is, there are much more demands for the photoreceptor that has a high sensitivity in repeat use and long span of life because a decline in the surface potential of the photoreceptor can be observed after repeating the above cycle several times. Thus these problems lead to a decline in image concentration with respect to the image qualities, resulting in being no fit for practical use.

It has not been known what was caused the deterioration but several factors may be related. For example it may be due to ozone, $No_x$, and other gases to be generated by means of corona discharge. The photoreceptor is usually exposed to the atmosphere caused by the corona discharge during the steps of charging the surface of the photoreceptor, transforming the developed toner on the photoreceptor to paper, and so on. Therefore, the photoreceptor may be gradually deteriorated by repeating the process of image formation, as a result of being affected by the above gases.

In general, the functionally distinguishable type photoreceptor is constructed so as to form a charge transport layer on a charge generation layer for the purpose of stabilizing its electrophotographic characteristics and making its life span longer. For this kind of the construction, the photoreceptor can be used in negative-charged condition where holes are transported as charge carriers by means of the organic charge transport material that has been currently used in practice. Therefore, a negative corona discharge is performed in the step of charging. However, the negative corona discharge leads to the generation of active gases such as ozone and $No_x$, much more than that in the positive corona discharge, and results in more serious problem of the above deterioration.

Thus the electrophotographic device is adversely affected by the above gases, so that the device generally comprises a means for exhausting gases around the corona discharger. In spite of using such means, however, it is very difficult to remove almost all the gases from the device.

For preventing the deterioration of the photoreceptor, therefore, various anti-oxidizing agents to be added in a photosensitive layer thereof have been proposed. For example hindered phenols are disclosed in Japanese Patent Application Laid-open No. 122444/1982 discloses the addition of hindered phenols, Japanese Patent Application Laid-open No. 143763/1986 discloses the method of adding hindered phenols in large quantities, and Japanese Patent Application Laid-open 105151/19887 discloses the hindered phenol having a specified structure. Besides the hindered phenols, Japanese Patent Application Publication No. 27693/1994 discloses hindered amines and Japanese Patent Application Publication discloses hindered amines and specified electron-acceptable compounds.

As described above, the anti-oxidizing agent prevents the deterioration of the photoreceptor to be caused by the active gases such as ozone and $NO_x$ to a certain extent. In recent years, however, there is a demand for more perfectly preventing the deterioration of the photoreceptor to serve the needs of the photoreceptor having its longer life span in the industrial field.

SUMMARY OF THE INVENTION

An object of the present invention is to provide a novel electrophotographic photoreceptor having a long-term life span and showing stable electric properties and good durabilities in repeat use in which a photoreceptor formed on a conductive substrate comprises a pigment as a photoconductive material, a binder resin, an organic charge transport material, and the like.

In a first aspect of the present invention, there is provided an electrophotographic photoreceptor comprising a conductive substrate and a photosensitive layer formed on the conductive substrate, wherein the photosensitive layer contains one selected from the group consisting of compounds respectively represented by the following formulae (I), (II), (III), (IV), and (V);

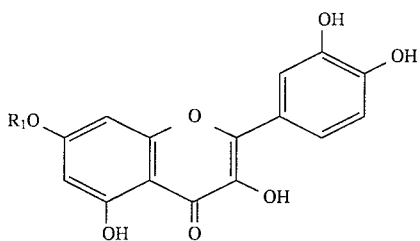

wherein $R_1$ stands for one selected from a hydrogen atom, an alkyl group, acyl group, and glycocyl group;

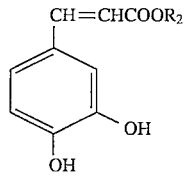

wherein $R_2$ stands for one selected from a hydrogen atom, an alkyl group which may optionally have a substituent(s), and an aryl group which may optionally have a substituent(s);

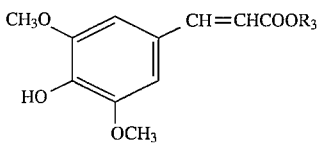

wherein $R_3$ stands for one selected from a hydrogen atom, an alkyl group which may optionally have a substituent(s), an aryl group which may optionally have a substituent(s);

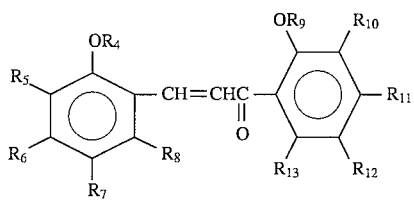

wherein each of $R_4$ to $R_{13}$ stands for one selected from a hydrogen atom, an alkyl group which may optionally have a substituent(s), an aryl group which may optionally have a substituent(s); and

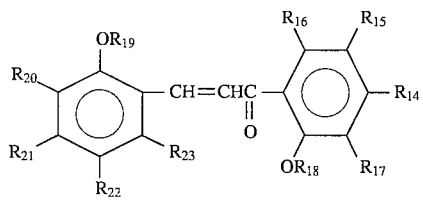

wherein each of $R_{14}$ to $R_{23}$ stands for one selected from a hydrogen atom, an alkyl group which may optionally have a substituent(s), an aryl group, alcorygroup, aroylgroup, or arylgroup which may optionally have a substituent(s).

An amount of the selected compound comprised in the photosensitive layer may be in the range of 0.1 to 30 percent, preferably of 1 to 20 percent by weight of the photosensitive layer.

The photosensitive layer may be of a single-layer structure comprising a charge generation material and a charge transport material.

The photosensitive layer may be of a multi-layered structure having a charge generation layer comprising a charge generation material and a charge transport layer comprising a charge transport material.

The selected compound may be comprised in the charge transport layer.

An electrophotographic photoreceptor may further comprise an under-coating layer between the conductive substrate and the photosensitive layer.

The under-coating layer may be a hardened film mainly comprising melamine resin, aromatic carboxylic acid and/or aromatic carboxylic anhydride, and iodine being fixed thereon.

The charge transport material may be a hydrazone compound represented by the formula (VI):

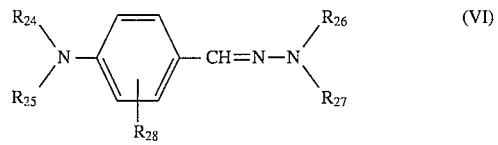

wherein each of $R_{24}$, $R_{25}$, $R_{26}$, and $R_{27}$ stands for selected from the group consisting of an alkyl group, an aralkyl group, and an aryl group, which may be substituted; and $R_{28}$ stands for an atom or a group selected from the group consisting of a hydrogen atom, a halogen atom, an alkyl group, and an alkoxy group, and $R_{24}$ and $R_{25}$ may be bound together to form a ring, and also $R_{24}$ or $R_{25}$ may be bound with $R_{28}$ to form a ring.

The charge transport material may be a distyryl compound represented by the formula (VII):

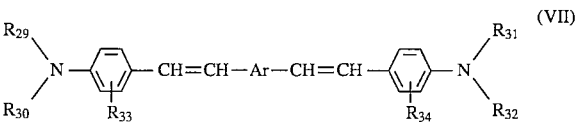

wherein each of $R_{29}$, $R_{30}$, $R_{31}$, and $R_{32}$ stands for one selected from the group consisting of an alkyl group and an aryl group, respectively, which may be substituted; each of $R_{33}$ and $R_{34}$ stands for an atom or a group selected from the group consisting of a hydrogen atom, a halogen atom, an alkyl group, and an alkoxy group, and Ar is an aryl group or an aromatic heterocyclic group.

DETAILED DESCRIPTION OF THE PREFERRED EMBODIMENTS

Figure 1:
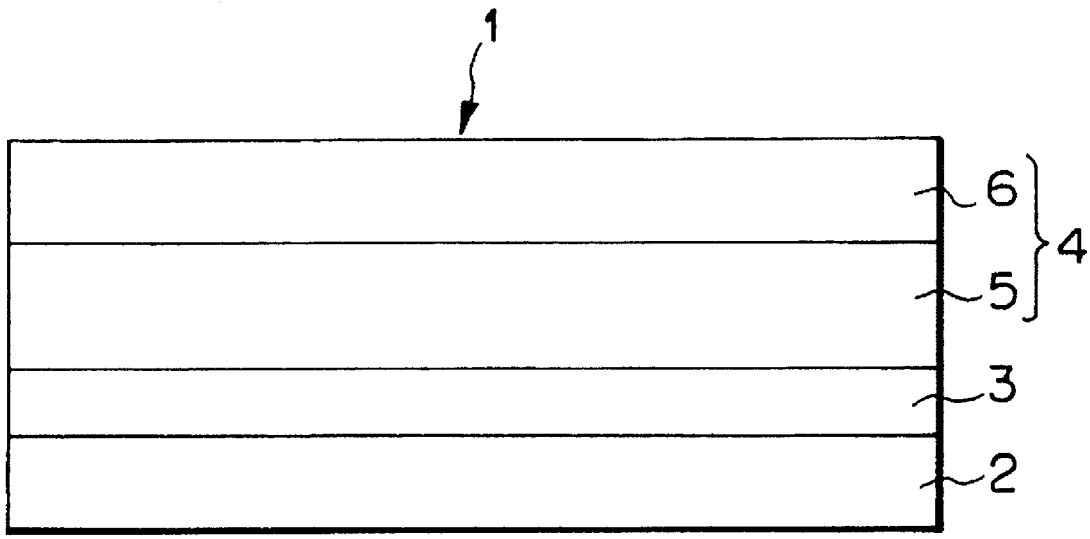
FIG. 1 is a schematic cross-sectional view of one of the preferred embodiments of the electrophotographic photoreceptor comprising an undercoat layer and a photosensitive layer, the latter consists of a charge generation layer and a charge transport layer, in accordance with the present invention.

In accordance with the present invention, an electrophotographic photoreceptor comprises one of the chemical compounds represented by the following formulae (I) to (V) in a photosensitive layer formed on a conductive substrate.

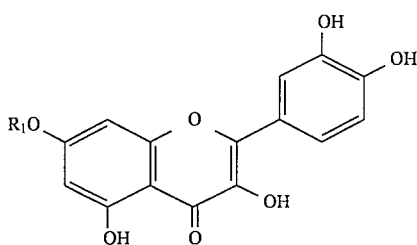

wherein $R_1$ stands for one selected from the group consisting of a hydrogen atom, an alkyl group, an acyl group, and a glycocyl group.

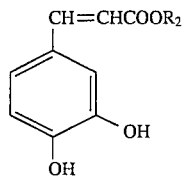

wherein $R_2$ stands for one selected from the group consisting of a hydrogen atom, an alkyl group optionally having a substituent, and an aryl group optionally having a substituent.

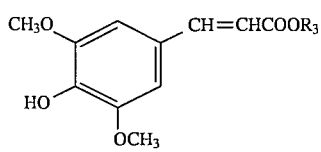

wherein $R_3$ stands for one selected from the group consisting of a hydrogen atom, an alkyl group optionally having a substituent(s), and an aryl group optionally having a substituent(s).

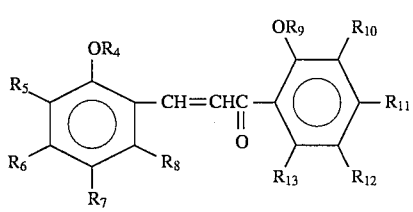

wherein each of $R_4$ to $R_{13}$ stands for one selected from the group consisting of a hydrogen atom, an alkyl group which may optionally have a substituent(s), and an aryl group optionally having a substituent(S).

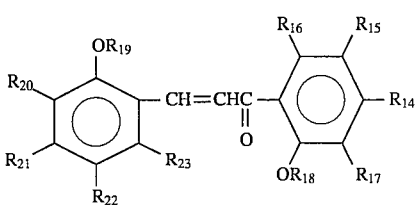

wherein each of $R_{14}$ to $R_{23}$ stands for one selected from the group consisting of a hydrogen atom, an alkyl group which may optionally have a substituent(s), and an aryl group which may optionally have a substituent(s).

The amount of the compound selected from the chemical compounds of formulae (I) to (V) to be comprised in the photosensitive layer is preferably in the range of 0.1 to 30 percent by weight of the photosensitive layer.

In the case of a function-separated type electrophotographic photoreceptor, the electrophotographic effects can be attained by adding one of the above chemicals compound in the charge generation layer or the charge transport layer. But it is preferable to include the above chemical compound in the charge transport layer.

The chemical compounds of the formula (I) will be represented more concretely by the following formulae.

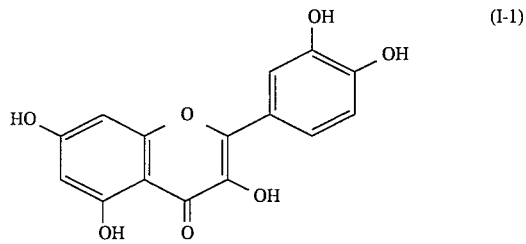

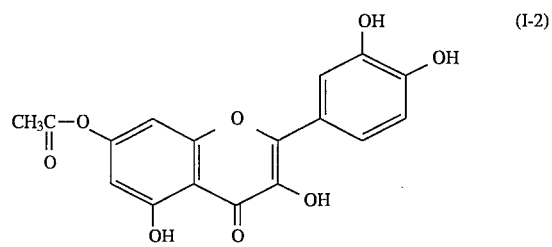

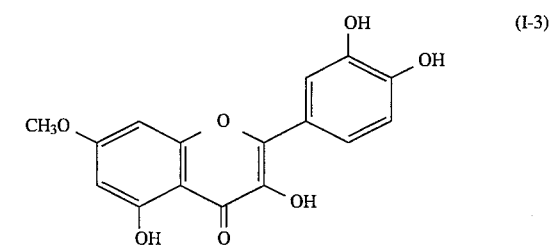

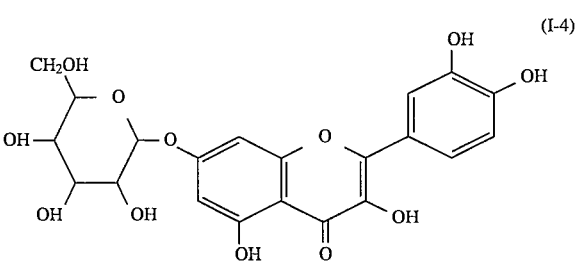

The chemical compounds of the formula (II) will be represented more concretely by the following formulae.

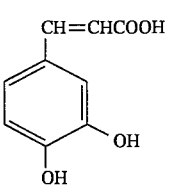

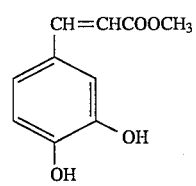

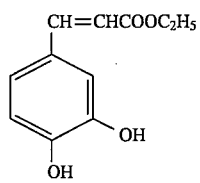

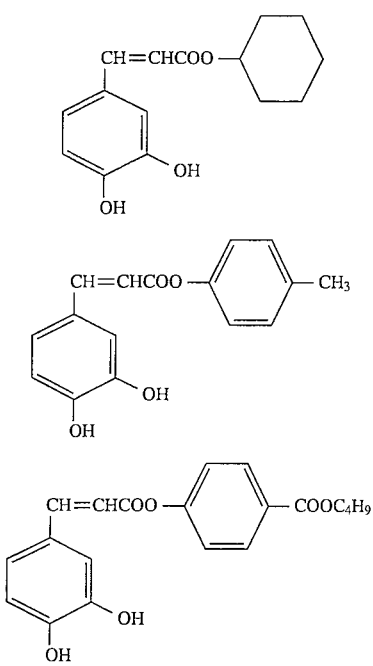

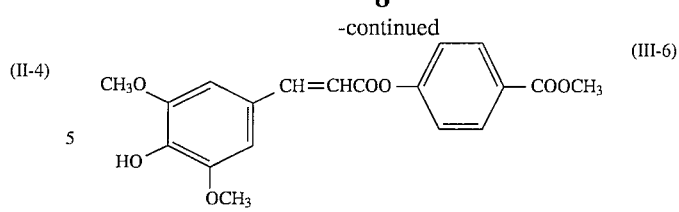

The chemical compounds of the formula (III) will be represented more concretely by the following formulae.

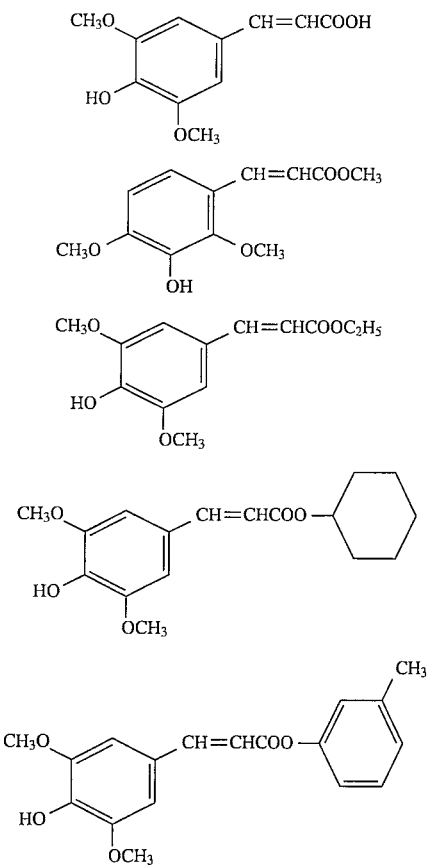

The concrete examples of the chemical compounds represented by the formula (IV) are the followings.

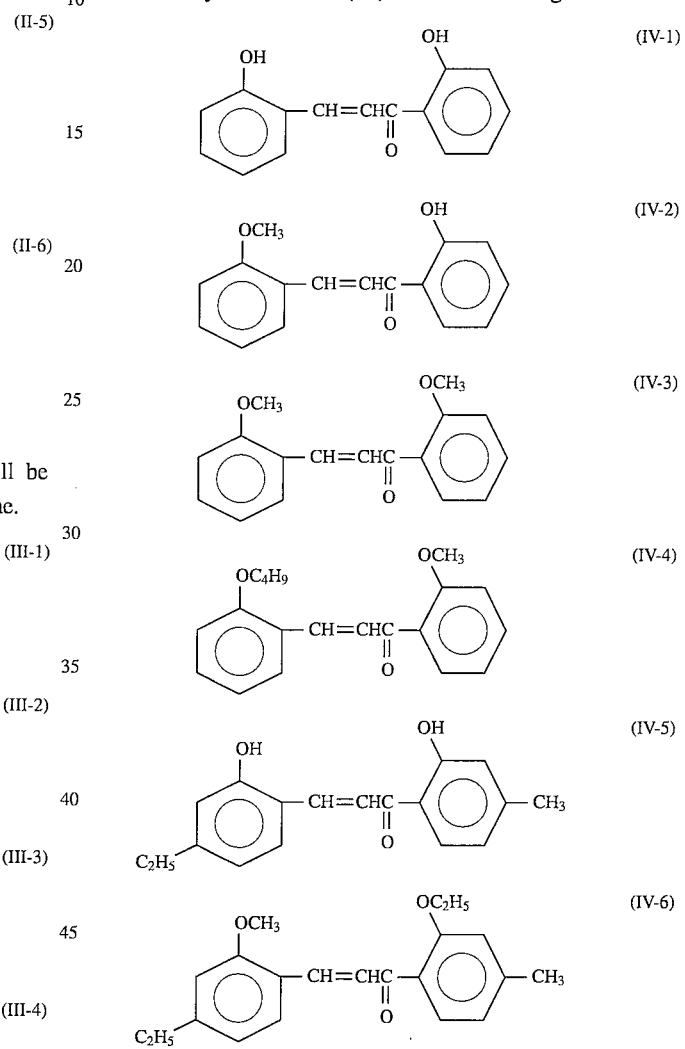

Furthermore, each chemical compound described above can be easily prepared by the condensation reaction between an appropriate salicylaldehyde derivative and an appropriate 2-hydroxylacetophenone derivative in alkali atmosphere.

The concrete examples of the chemical compounds represented by the formula (V) are the followings.

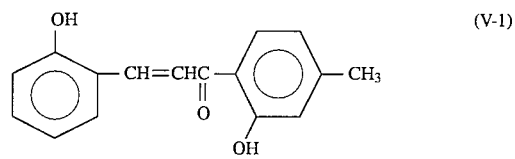

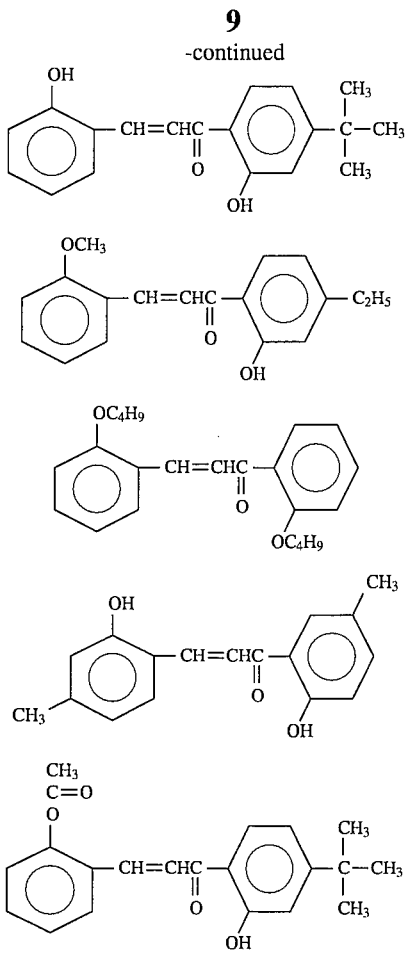

The above chemical compounds can be easily prepared by the esterification reaction between an appropriate benzalacetic acid derivative and an appropriate catechol derivative.

By means of adding one of the chemical compounds represented by the formulae (I) to (V) in the photosensitive layer, the deterioration thereof to be caused by the harmful influences of the active gases such as ozone and $No_x$ as a result of the corona discharge can be suppressed. The amount of the compound to be added in the photosensitive layer is preferably in the range of 0.1 to 30 percent, more preferably in the range of 1 to 20 percent by weight of the whole amount of the photosensitive layer. When the addition amount is less than that range, the photoreceptor can be deteriorated by the above active gases. When the addition amount is over than that range, on the other hand, the photoreceptor can be of poor electrophotographic characteristics, such as poor sensitivities.

Figure 2:
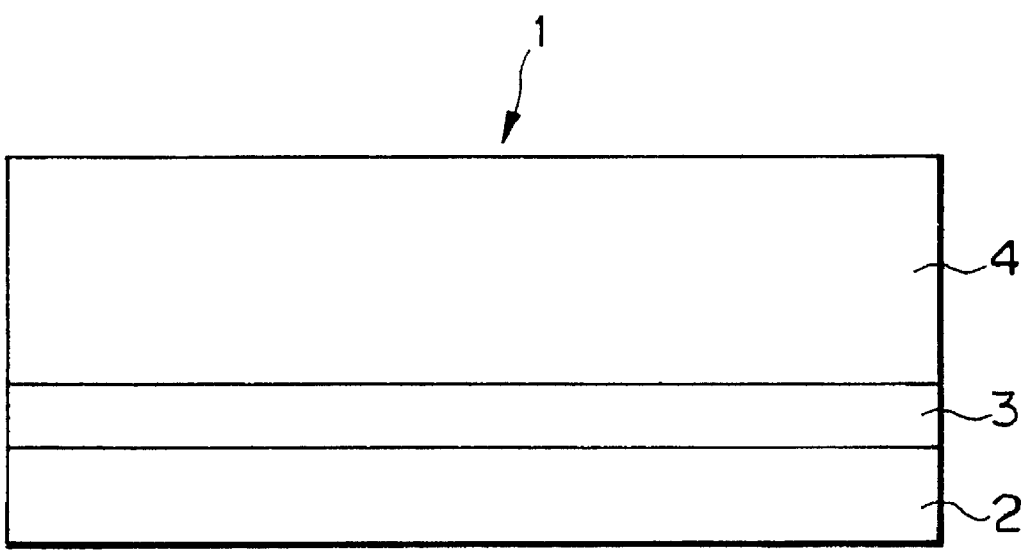
FIG. 2 is a schematic cross-sectional view of one of the preferred embodiments of the electrophotographic photoreceptor comprising an undercoat layer and a single-layered photosensitive layer.

FIG. 1 is a preferred embodiment of the electrophotographic photoreceptor in accordance with the present invention. The electrophotographic photoreceptor 1 is in the type of having functionally distinguishable layers. That is, an under-coating layer 3 is formed on an conductive substrate 2 and then a charge generation layer 5 and a charge transport layer 6 are stacked on the under-coating layer 3 in that order to form a photosensitive layer 4. As shown in FIG. 2, by the way, the present invention is not limited to the type of having functionally distinguishable layers but also possible to the type of having a single layer that performs both steps of generating and transporting charges.

In the present invention, the conductive substrate 2 is in the form of a metallic drum or sheet made of a metal such as aluminum, nickel, copper, and stainless steel, or an alloy made by mixing together two or more different metals; a drum or sheet made of a conductive resin; a drum or sheet of a non-conductive material such as glass, paper, or plastics, in which a surface thereof is covered with a conductive sheet or a metal deposition, or coated with a conductive paint. If necessary, the surface of the drum or sheet can be further subjected into the treatment of oxidation, ozone, UV, plasma, chemical agent, or the like. If necessary, furthermore, an under-coating layer 3 of soluble nylon, casein, polyvinyl alcohol, urethane, or the like may be formed on the surface of the conductive substrate.

It is preferable to prepare the under-coating layer 3 as a film made of a metal oxide such as alumite; a film made of a film-formable high-molecular, for example one selected from polyamides such as nylon 6, nylon 66, nylon 11, nylon 610, copolymerized nylon, and alkoxymethylated nylon, or selected from casein, polyvinyl alcohol, ethylene acrylate copolymer, gelatin, and polyvinyl butyral; and a resin film with dispersed conductive-, semiconductive-, or dielectric particles made of metal oxide such as zinc oxide or titanium oxide, aluminum oxide, silicon nitride, silicon carbide, carbon black, or the like.

The photosensitive layer 4 to be formed on the conductive substrate 2 through the under-coating layer 3 can be selected from the prior art photosensitive layers, for example a photosensitive layer of charge-transport complex prepared by mixing polyvinyl carbazole with trinitrofluoreon as disclosed in U.S. Pat. No. 3,484,237, a pigment-sensitized type photosensitive layer as disclosed in Japanese Patent Application publication No. 25658/1973, a single-layered type photosensitive layer prepared by dispersing a pigment into a hole-transport agent or a charge-transport agent as disclosed in Japanese Patent Application laid-open Nos. 30328/1972 and 18545/1972, a functionally distinguishable photosensitive layer mainly comprising a charge generation layer and a charge transport layer as disclosed in Japanese Patent Application laid-open No. 205537/1974. Among these photosensitive layers, the functionally distinguishable one is preferably applied in the photoreceptor of the present invention. Because the photoreceptor having excellent characteristics can be obtained with a big possibility by arranging the most appropriate materials for the function of each sub-layer of the photosensitive layer and combining appropriate sub-layers together. In addition, the photoreceptor having the high sensitivity with respect to exposure light to be used in the process of electrophotography.

The charge generation layer 5 is formed by the method for evaporating a thin film of charge generation material onto a surface of the under-coating layer formed on the substrate or by the way of applying a coating solution thereon and drying the coated solution. The coating solution is prepared by dispersing and dissolving a charge generation material and an appropriate binding agent in a solvent. The charge generation material to be used can be selected from non-organic charge generation materials such as selenium-tellurium and selenium-arsenic and organic charge generation materials such as azo pigment, disazo pigment, perynon pigment, perylene pigment, anthanthrone pigment, phtalocyanine pigment, pyrylium pigment, and squarylium pigment.

The above binding agent is not limited if it shows the properties of electrical insulation and membrane-formation. Preferably it may be selected from polyvinyl resin (e.g., polyvinyl formal, polyvinyl acetal, and polyvinyl butyral), acryl resin, polyester resin, polycarbonate resin, vinyl chloride copolymer resin, vinyl acetate copolymer resin, silicon resin, and so on. It is preferable that the binder agent occupies 20 to 90 percent by weight of the charge generation layer in preparation for the charge generation material. If necessary, an additional agent can be further included in the charge generation layer with the binder agent. The additional agent is, for example, a flexibilizer such as haloganated paraffin and tert-phenyl, and a pin-hole preventing agent such dimethyl phthalate.

The inorganic or organic charge generation material is blended with the above binder agent and the additional agent in the solvent and then applied on the under-coating layer by one of the techniques of dip-coating, splay-coating, and the like, by using an attritor, a sand mill, a paint shaker, or the like, so as to provide a dry thickness of the charge generation layer within the range of 0.01 µm to 5 µm.

The charge transport layer 6 is formed as a layer comprising a material with the ability of transporting charge carriers. That is, a charge transport material selected from styryl compounds, enamine compounds, hydrazone compounds, amine compounds, and so on is mixed with a mutually soluble resin such as polyester, polycarbonate, polymethacrylate ester, and polystyrene to prepare a coating solution. Then the coating solution is applied on a surface of the charge generation layer to form the charge transport layer with a thickness of 10 to 40 µm. It is possible to change the order of forming the charge generation layer and the charge transport layer on the substrate through the under-coating layer. The photoreceptor can be used in the positive charged condition when these layers are laminated in the reverse order.

A preferable hydrazone compound is indicated by the general formula (VI) below.

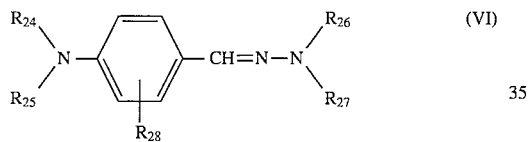
(VI)

wherein each of $R_{24}$, $R_{25}$, $R_{26}$, and $R_{27}$ stands for one selected from the group consisting of of an alkyl group, an aralkyl group, and an aryl group, which may be optionally substituted, respectively; and $R_{28}$ stands for one selected from the group consisting of a hydrogen atom, a halogen atom, an alkyl group, and an alkoxy group.

In the formula (VI), $R_{24}$ and $R_{25}$ may be optionally bound together to form a ring, and also $R_{24}$ or $R_{25}$ may be optionally bound with $R_{28}$ to form a ring.

The concrete examples of the hydrazon compound is represented by the following formulae (VI-1) to (VI-18).

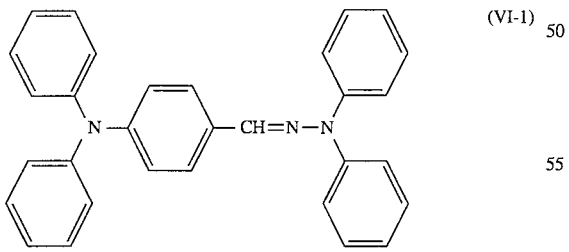
(VI-1)

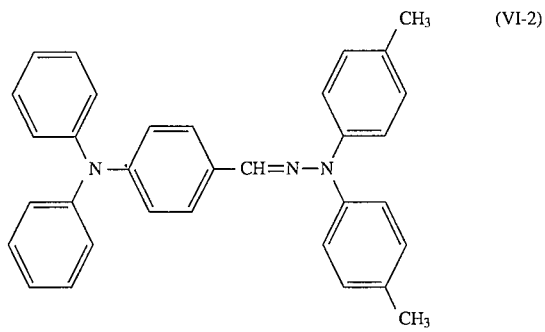
(VI-2)

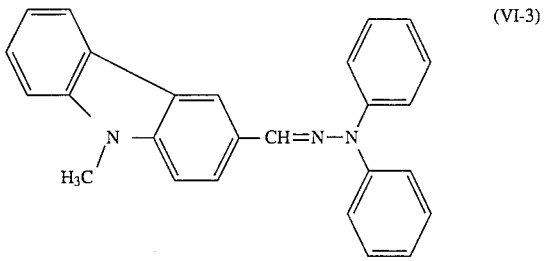
(VI-3)

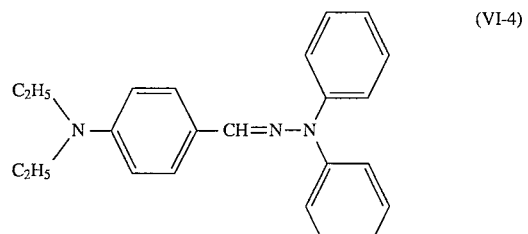
(VI-4)

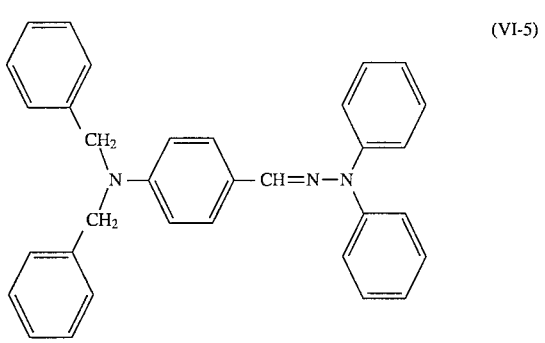
(VI-5)

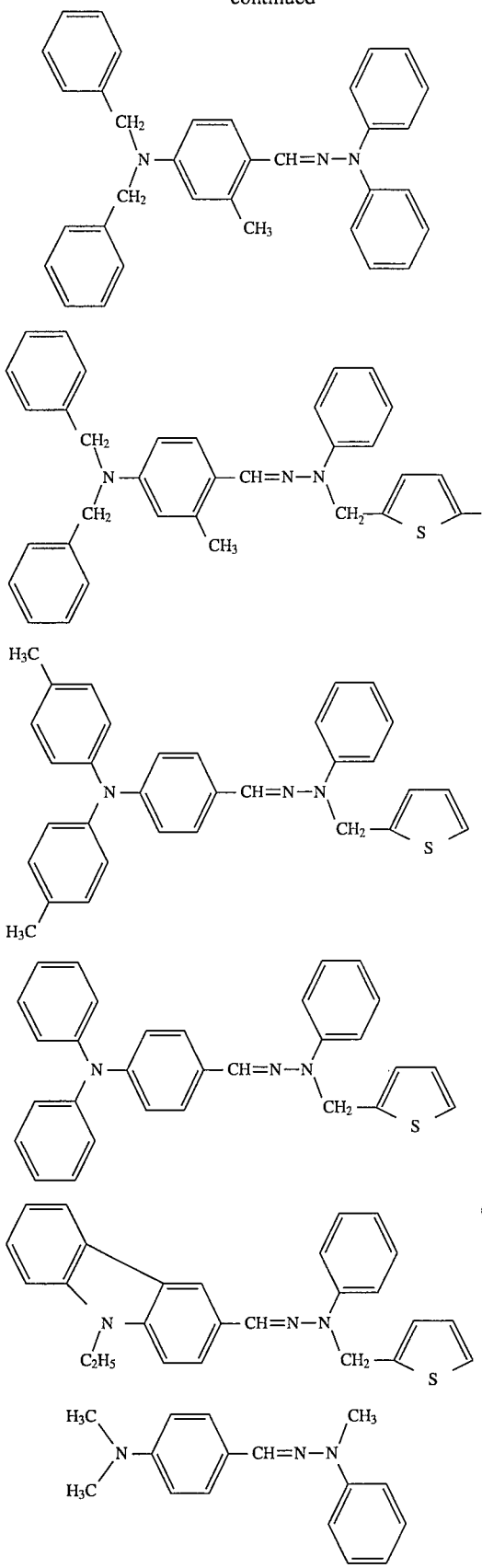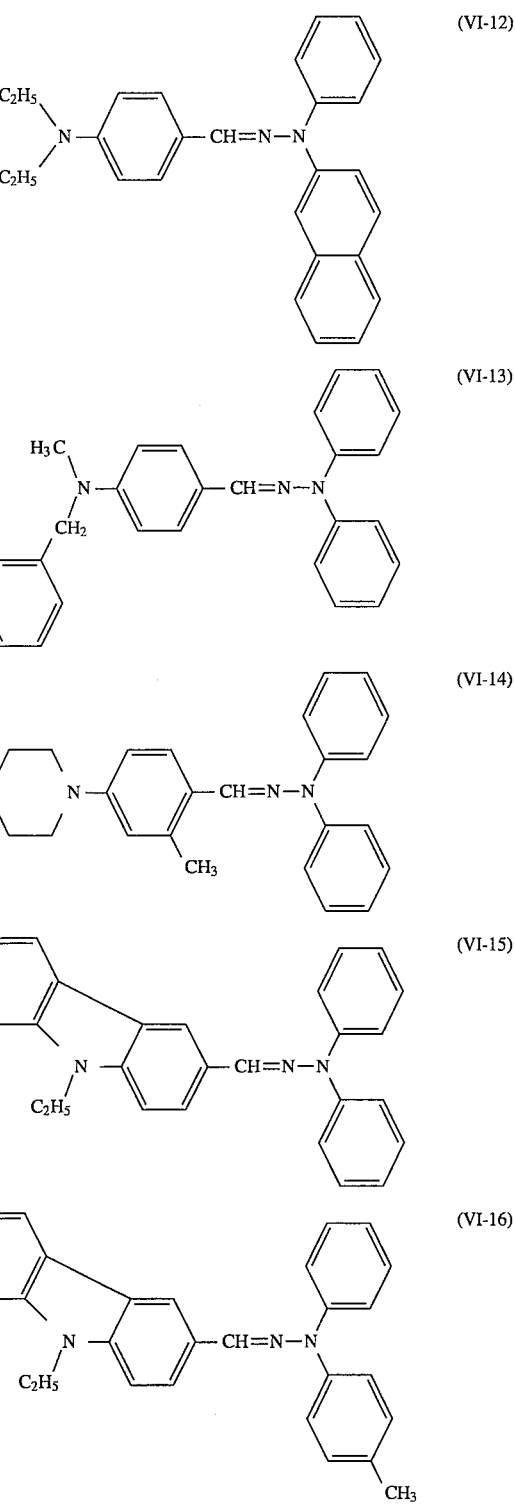

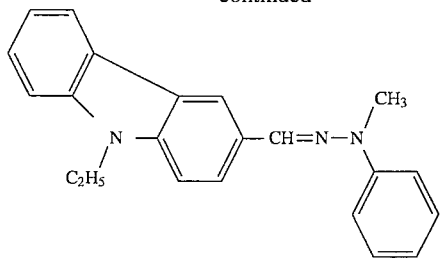

(VI-17)

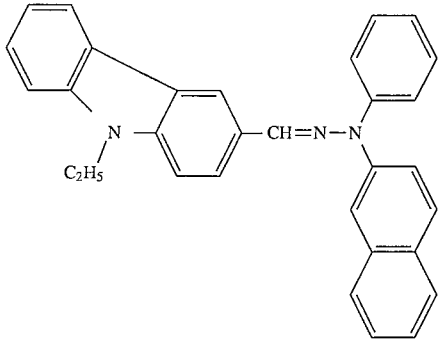

(VI-18)

A preferable distyryl compound is indicated by the general formula (VII) below.

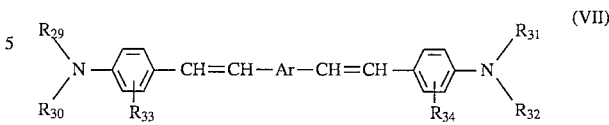

(VII)

wherein $R_{29}$, $R_{30}$, $R_{31}$, and $R_{32}$ are selected from an alkyl group and an aryl group, respectively, which may be optionally substituted; $R_{33}$ and $R_{34}$ are an atom or a group selected from a hydrogen atom, a halogen atom, an alkyl group, and an alkoxy group, respectively and Ar is an aryl group or an aromatic heterocyclic group.

The concrete examples of the hydrazon compound is represented by the following formulae (VII-1) to (VII-96).

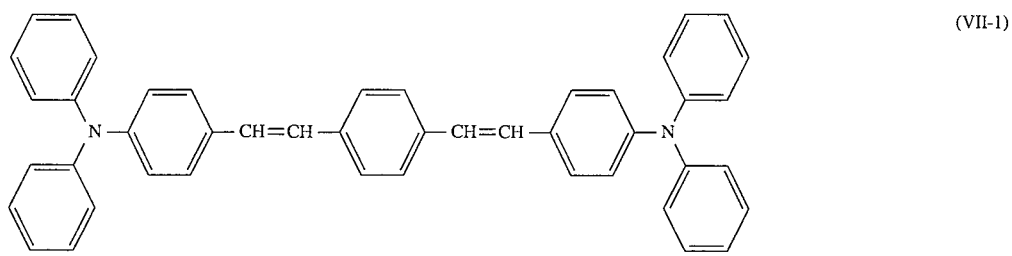

(VII-1)

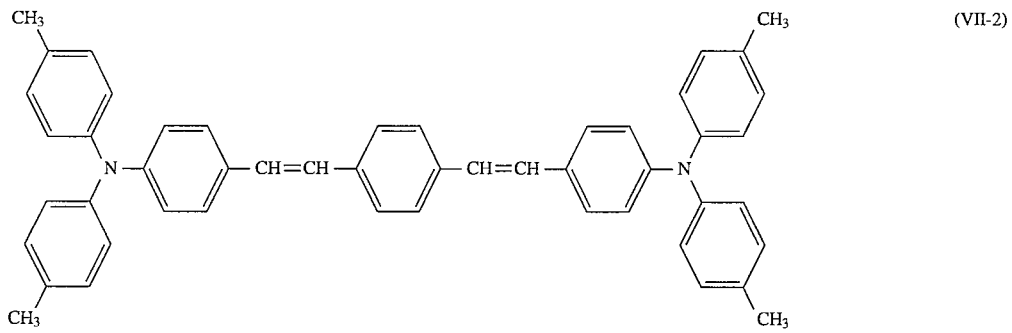

(VII-2)

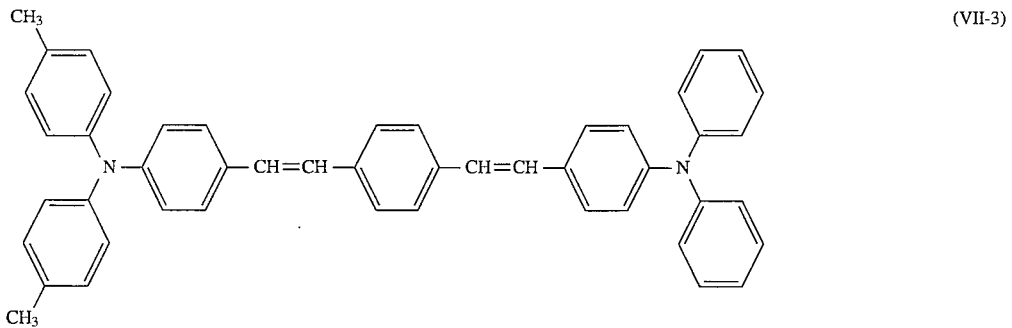

(VII-3)

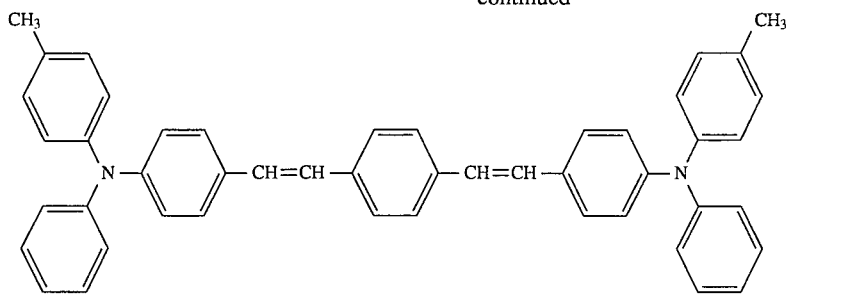
(VII-4)
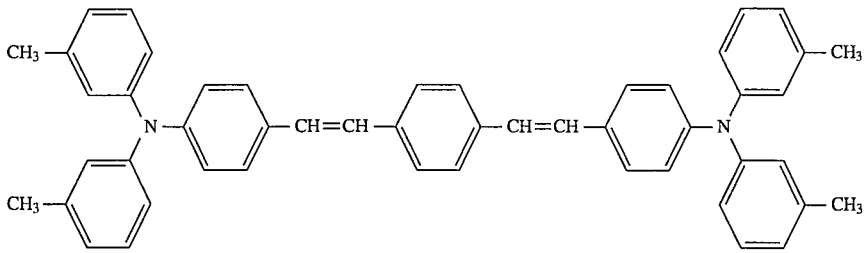
(VII-5)
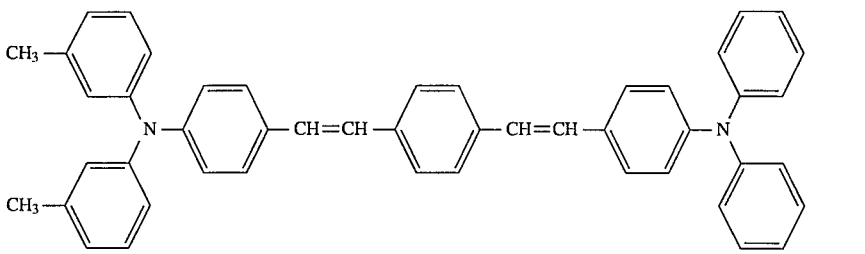
(VII-6)
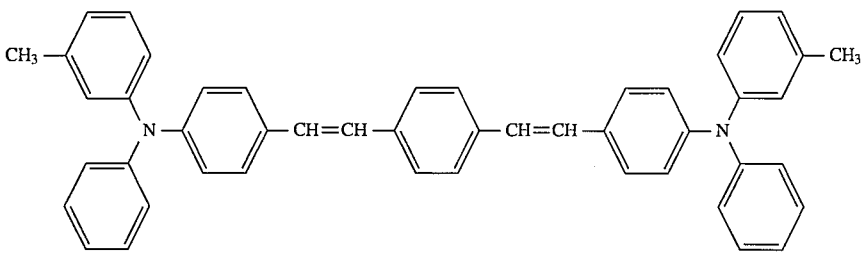
(VII-7)
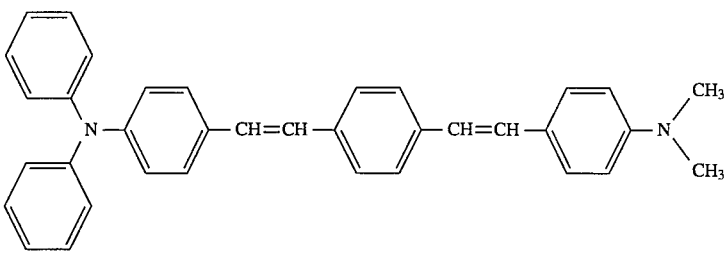
(VII-8)
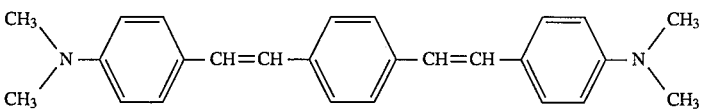
(VII-9)
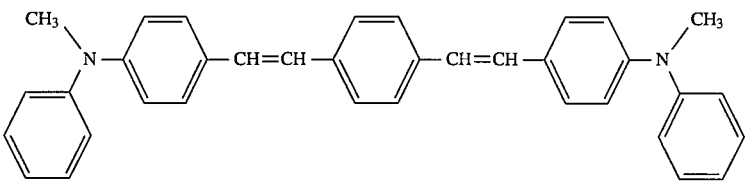
(VII-10)

-continued
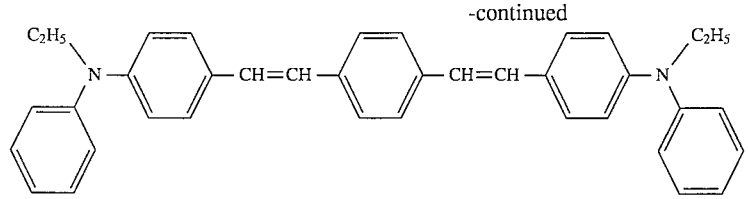 (VII-11)
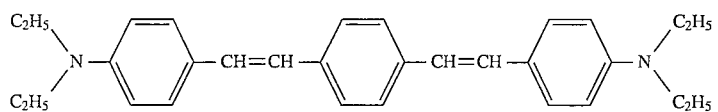 (VII-12)
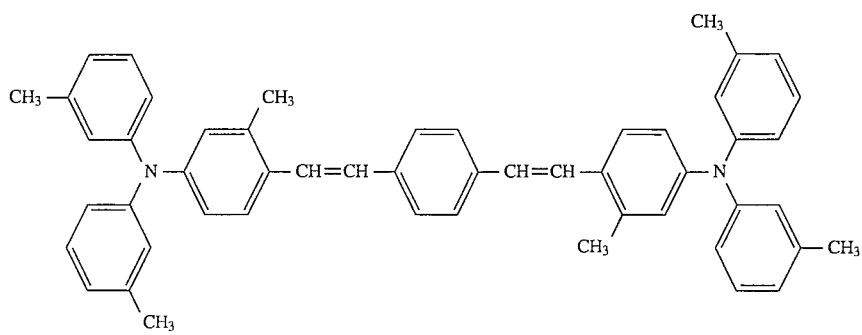 (VII-13)
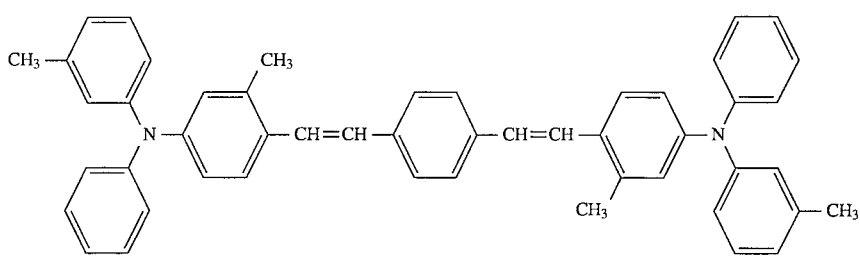 (VII-14)
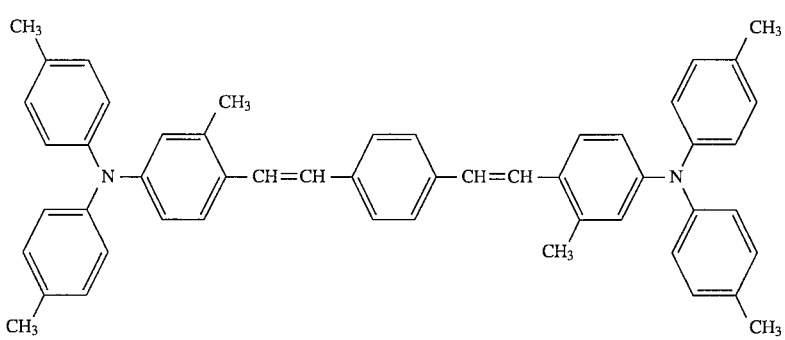 (VII-15)
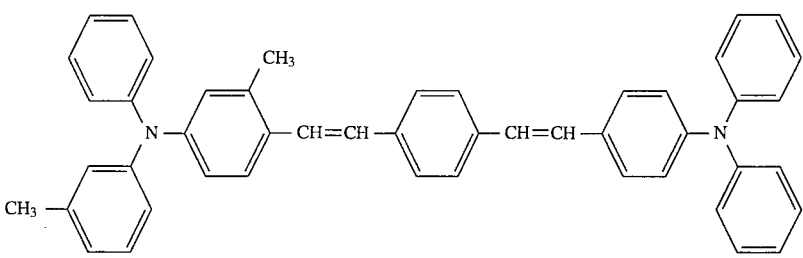 (VII-16)

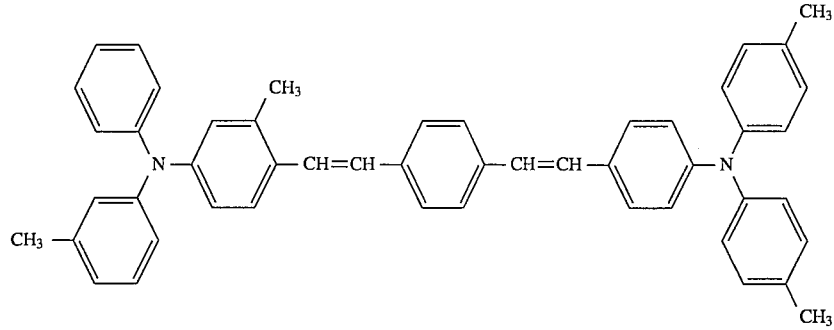
(VII-17)
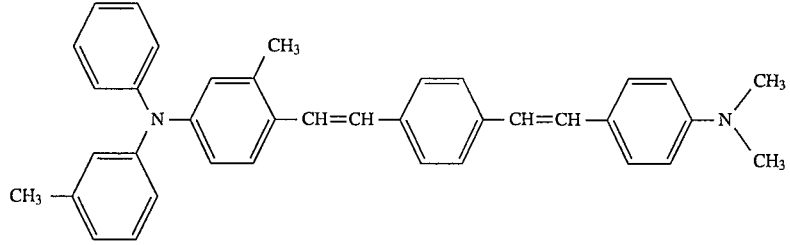
(VII-18)
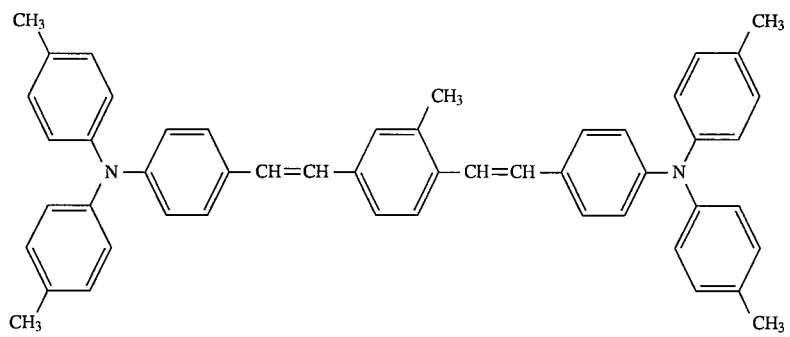
(VII-19)
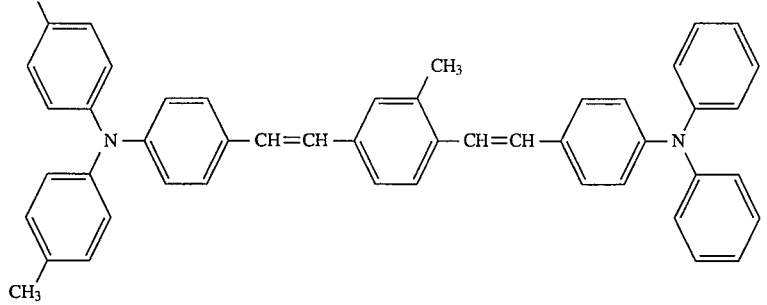
(VII-20)
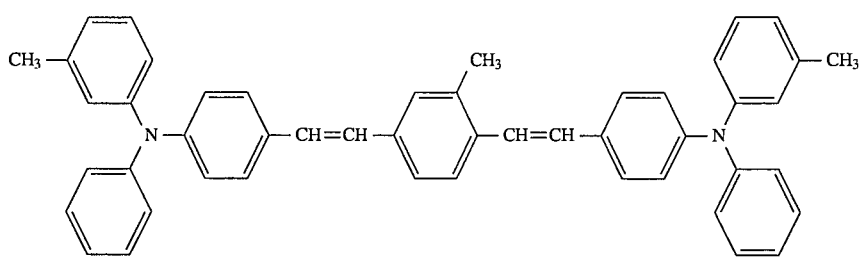
(VII-21)

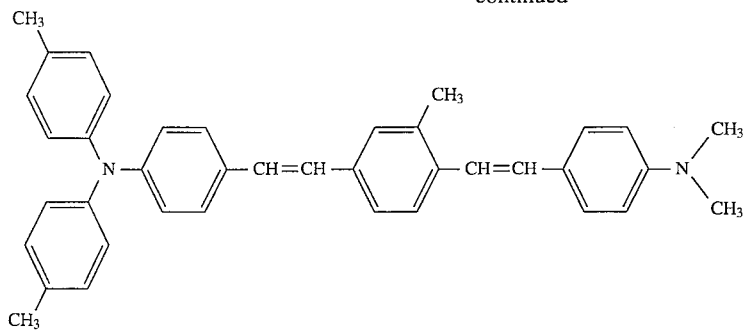
(VII-22)
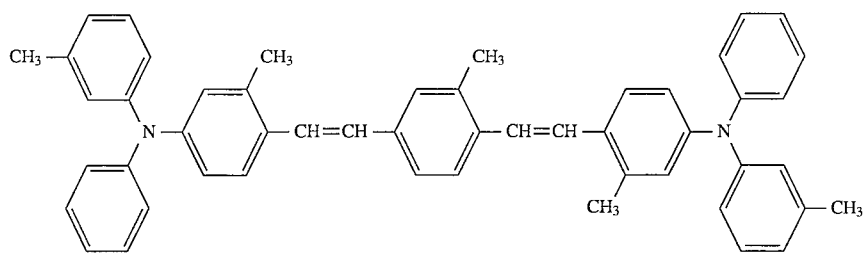
(VII-23)
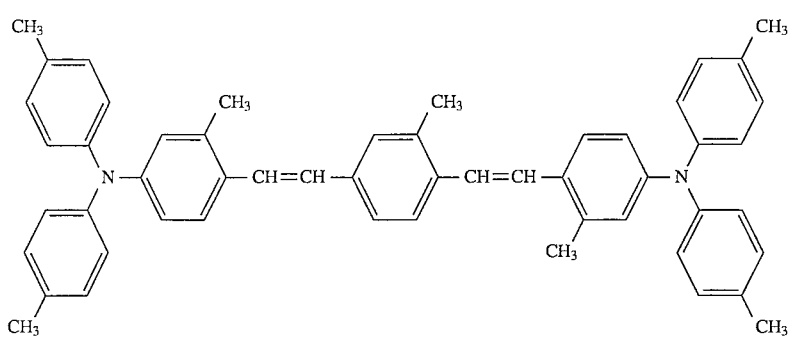
(VII-24)
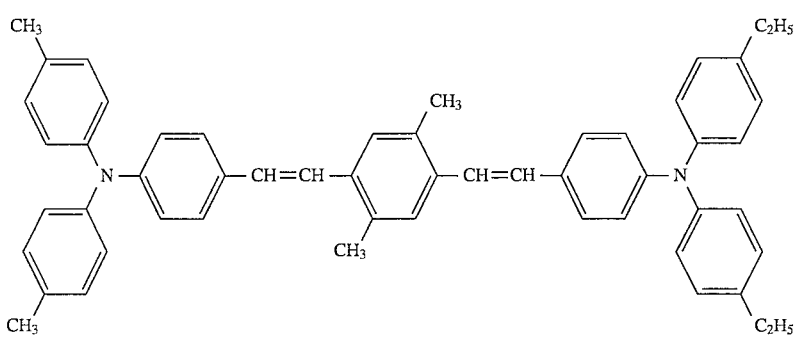
(VII-25)
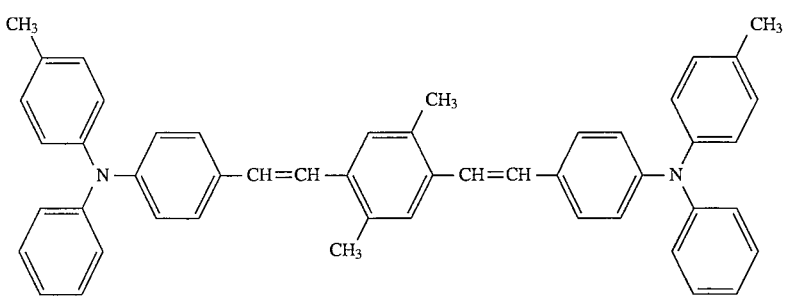
(VII-26)

-continued
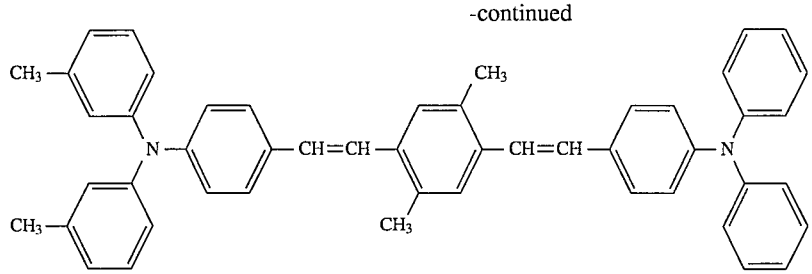
(VII-27)
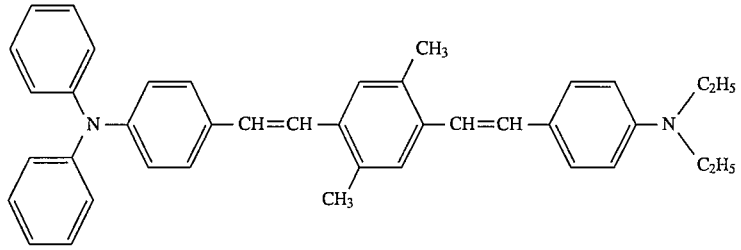
(VII-28)
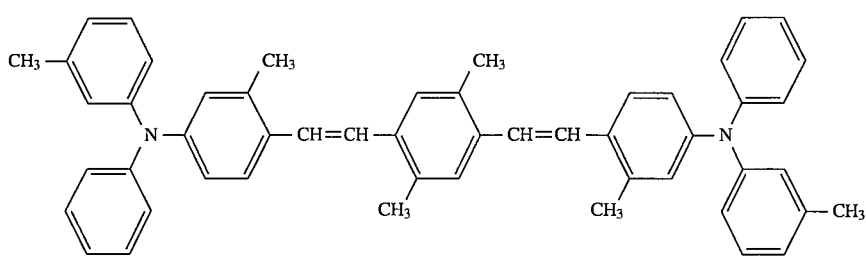
(VII-29)
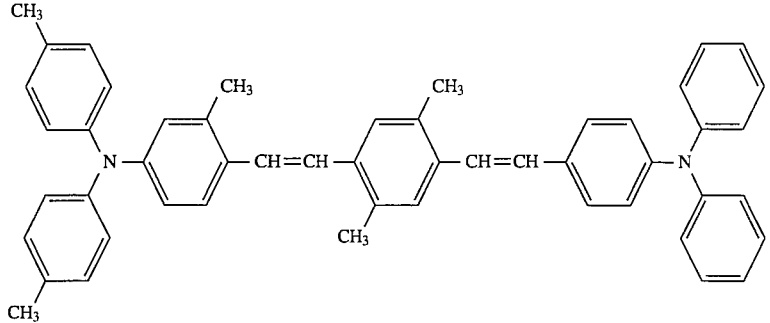
(VII-30)
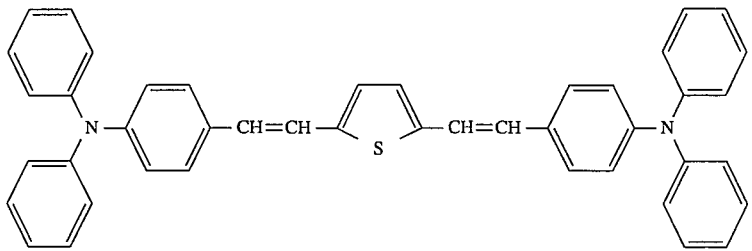
(VII-31)
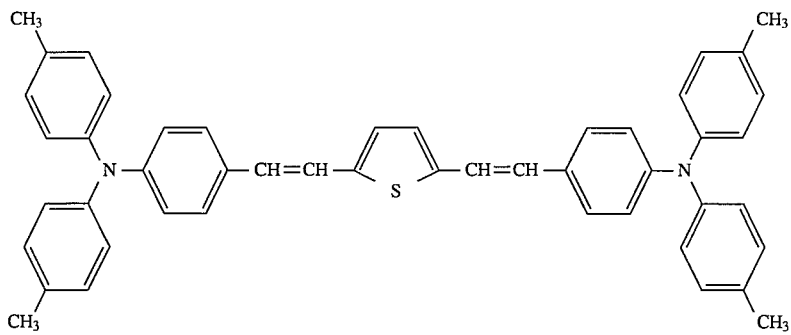
(VII-32)

-continued
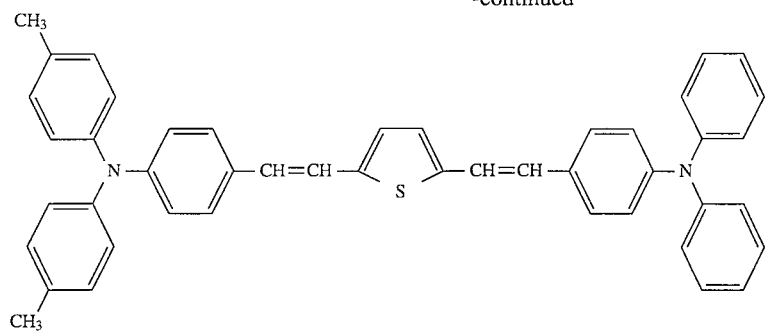
(VII-33)
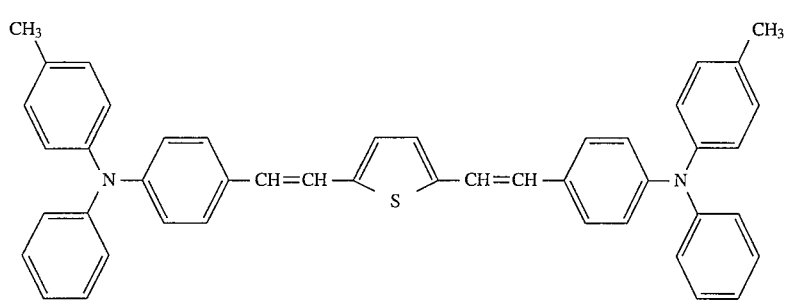
(VII-34)
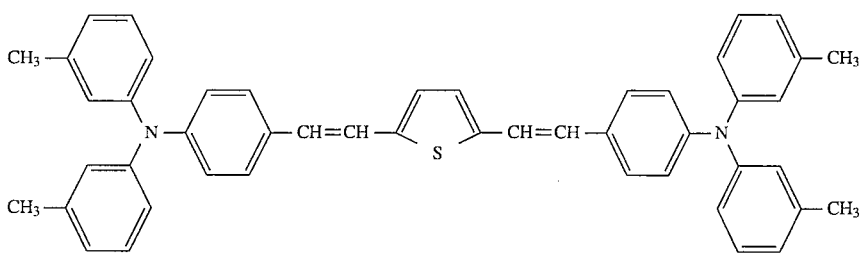
(VII-35)
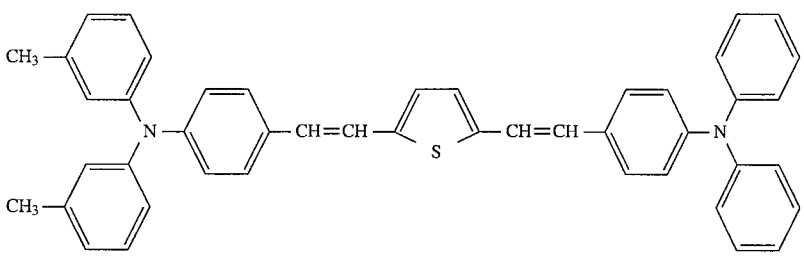
(VII-36)
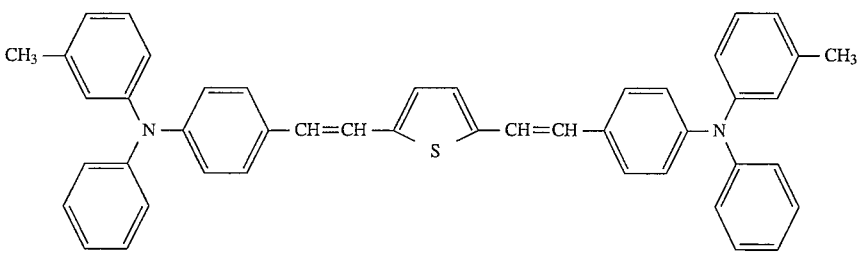
(VII-37)
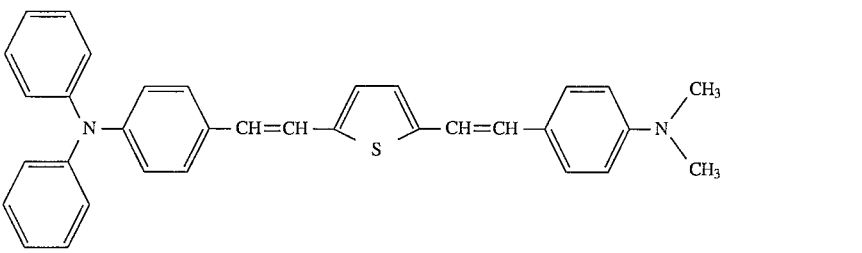
(VII-38)

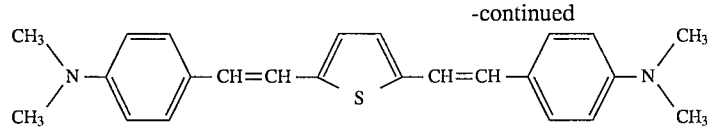  (VII-39)
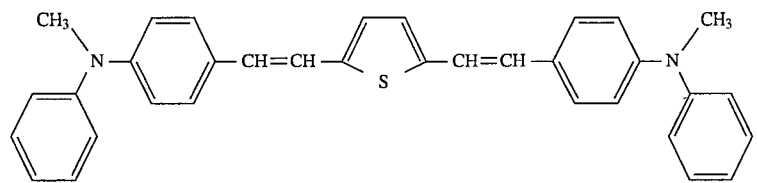  (VII-40)
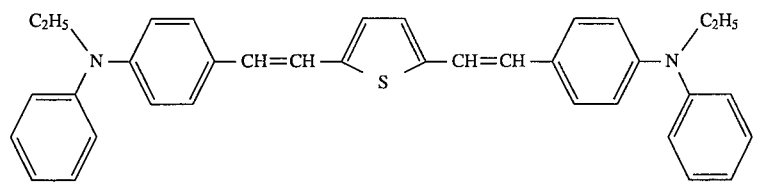  (VII-41)
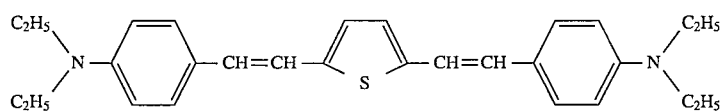  (VII-42)
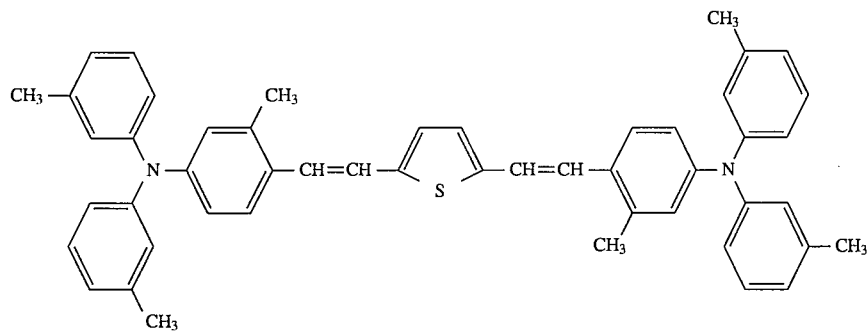  (VII-43)
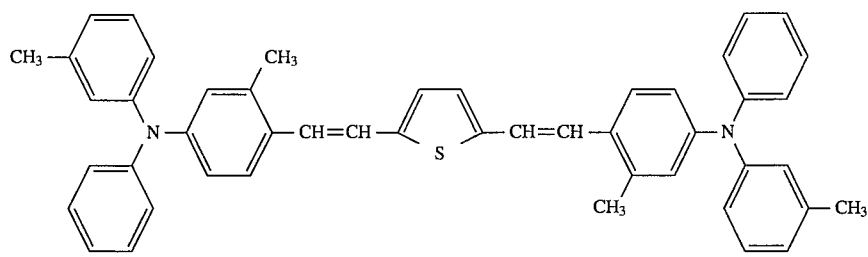  (VII-44)
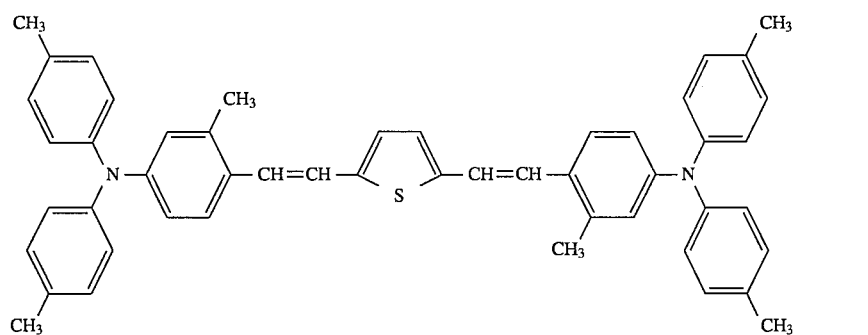  (VII-45)

-continued
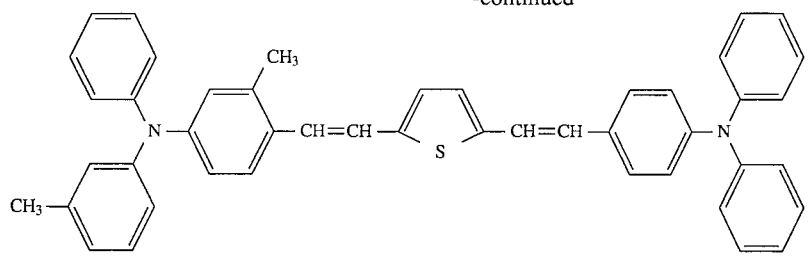
(VII-46)
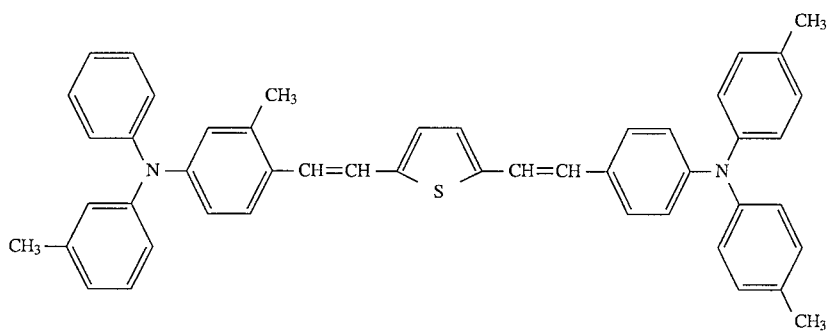
(VII-47)
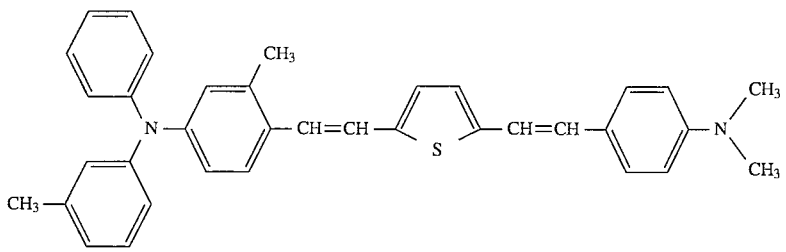
(VII-48)
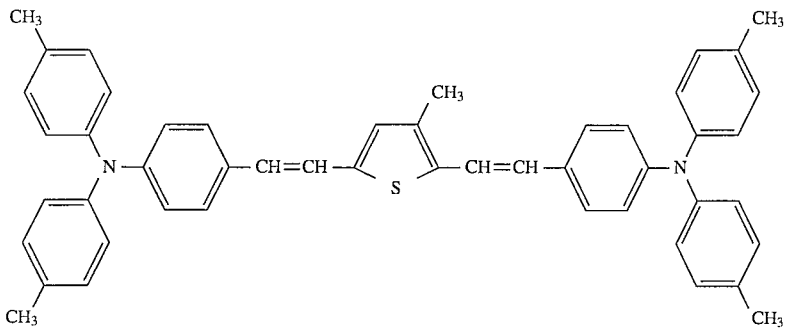
(VII-49)
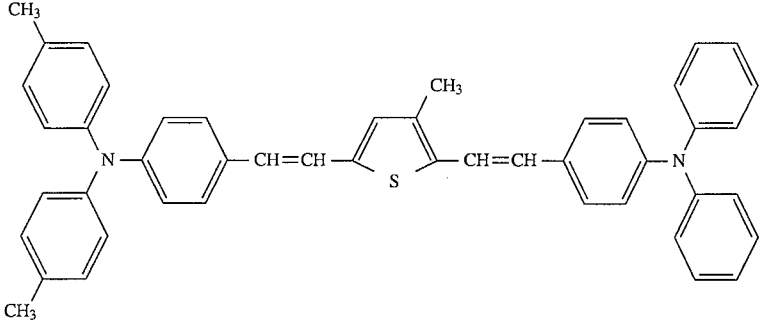
(VII-50)

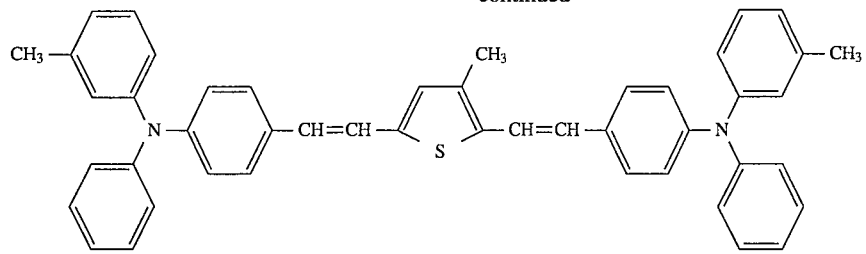
(VII-51)
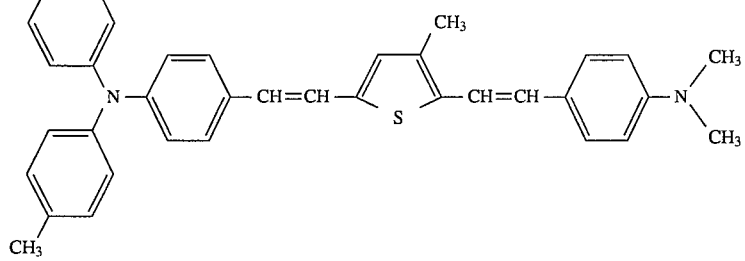
(VII-52)
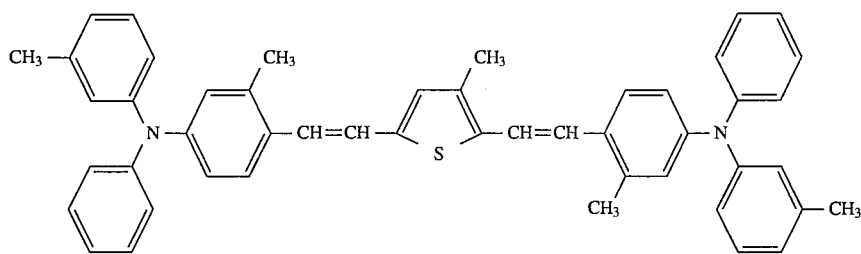
(VII-53)
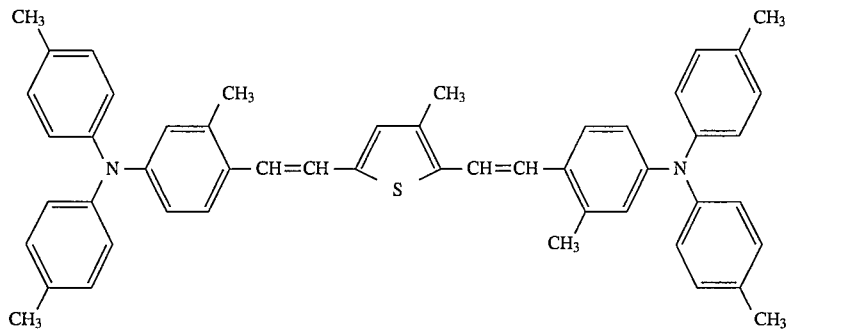
(VII-54)
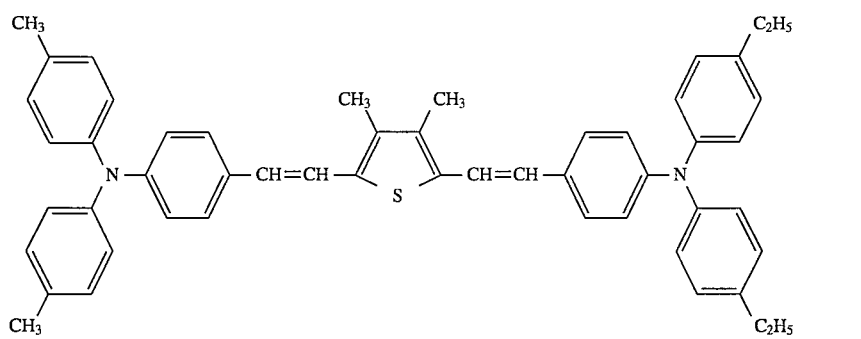
(VII-55)

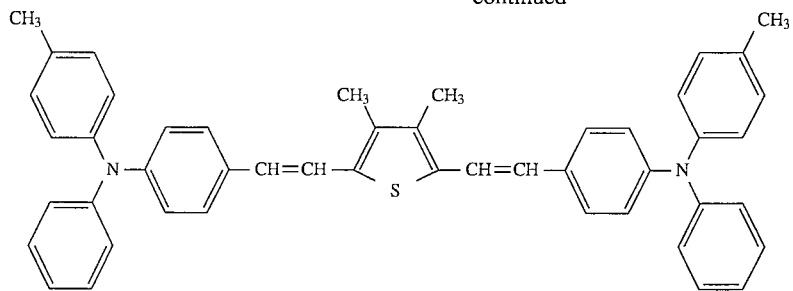
(VII-56)
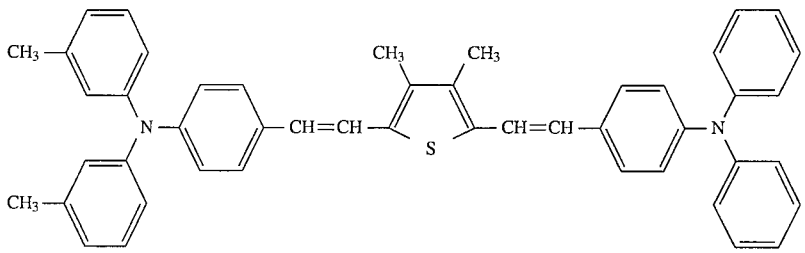
(VII-57)
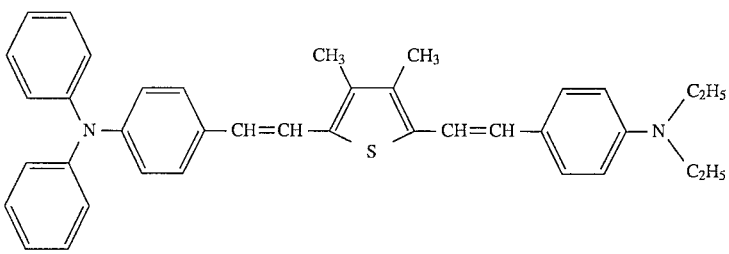
(VII-58)
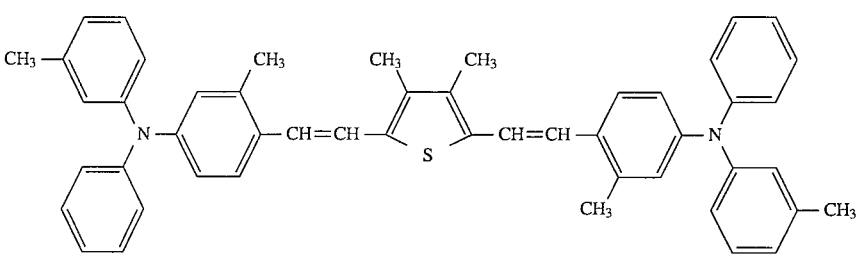
(VII-59)
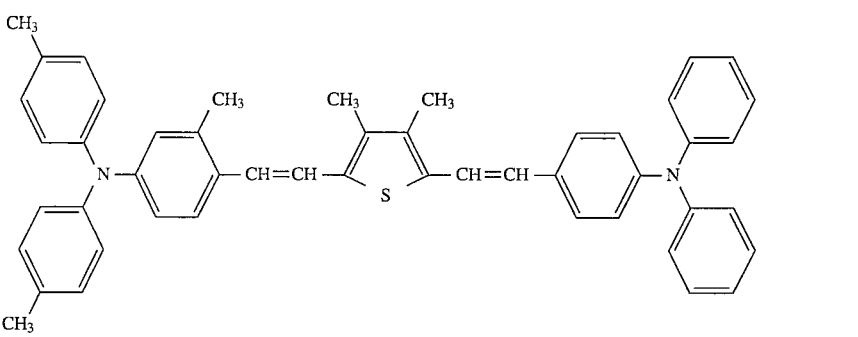
(VII-60)
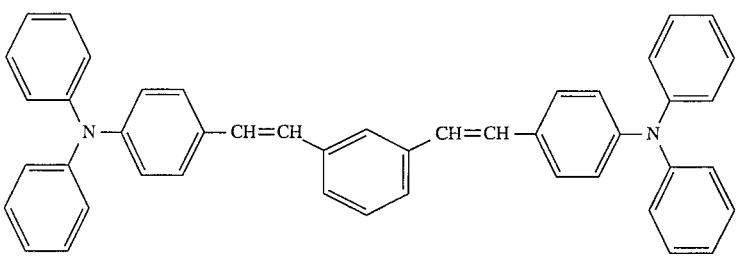
(VII-61)

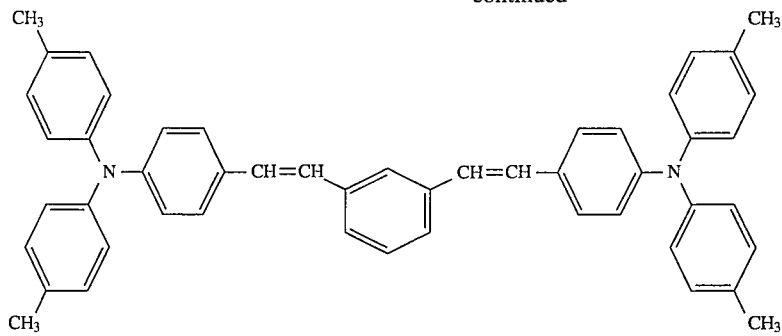
(VII-62)
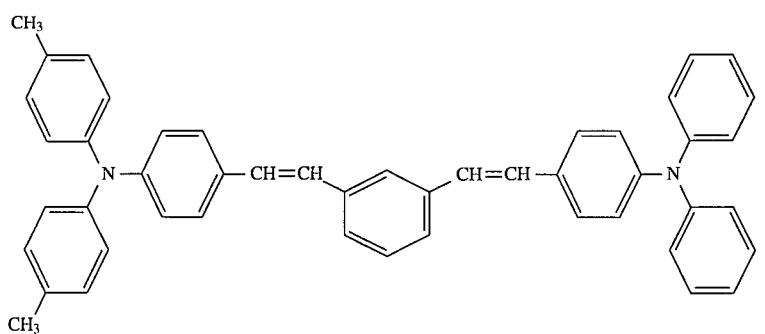
(VII-63)
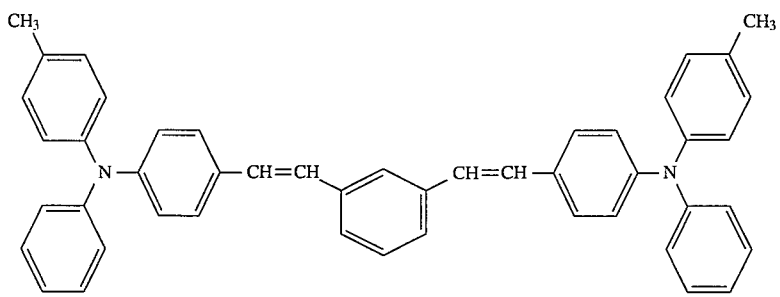
(VII-64)
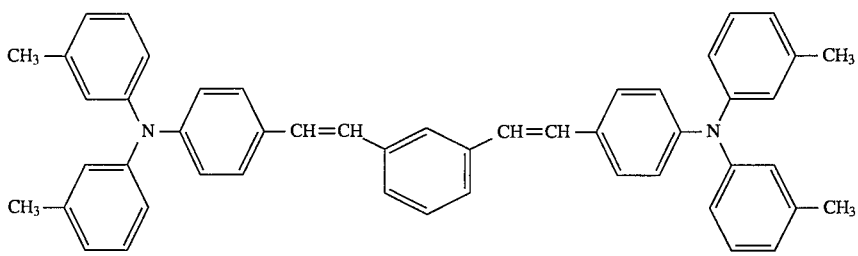
(VII-65)
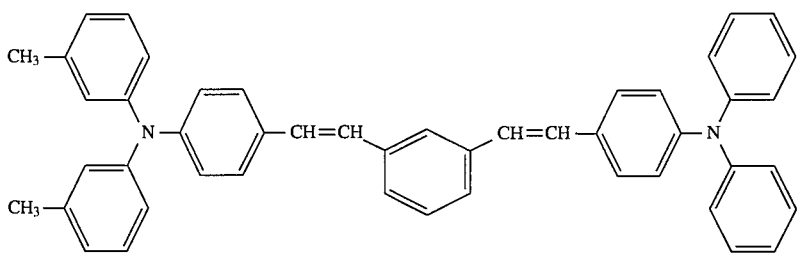
(VII-66)

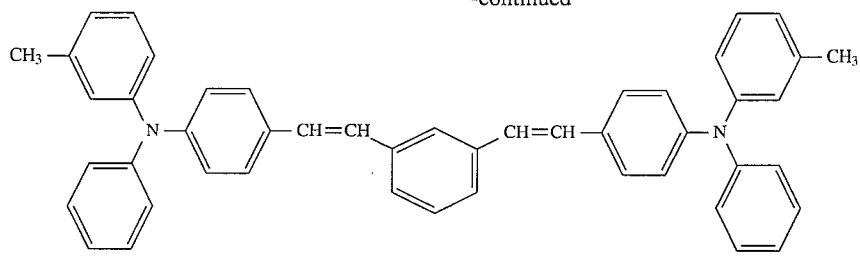
(VII-67)
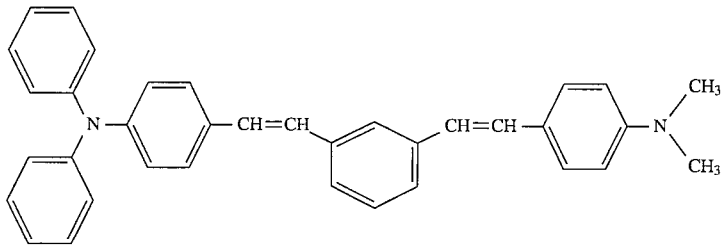
(VII-68)
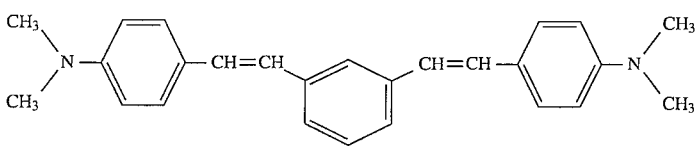
(VII-69)
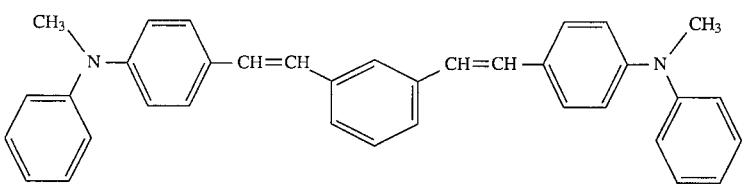
(VII-70)
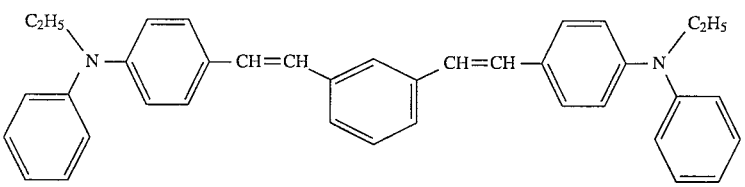
(VII-71)
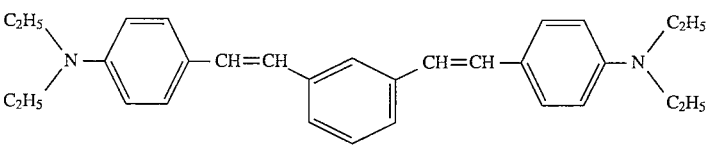
(VII-72)
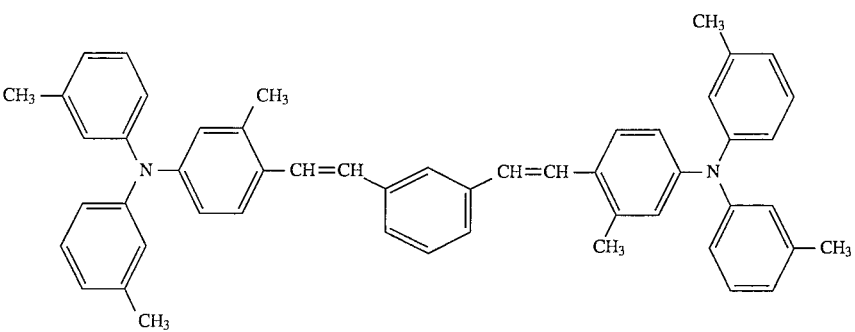
(VII-73)

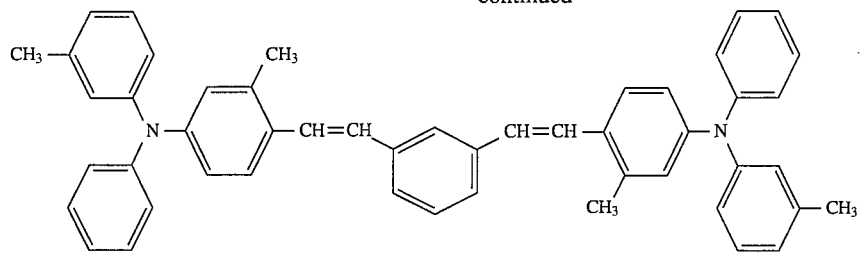
(VII-74)
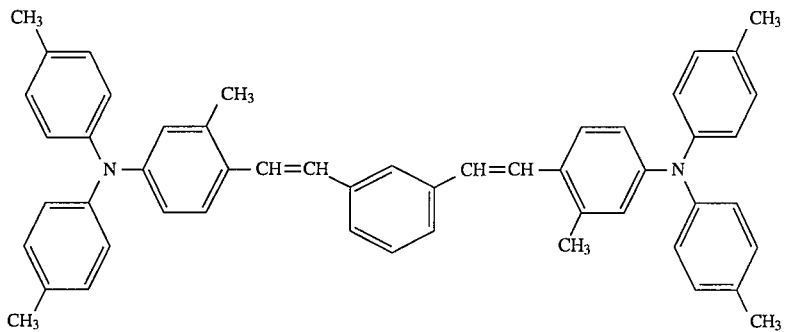
(VII-75)
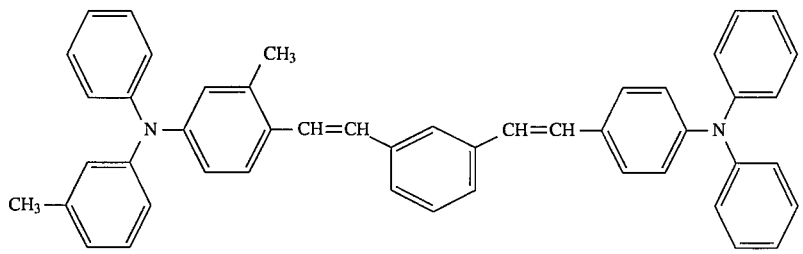
(VII-76)
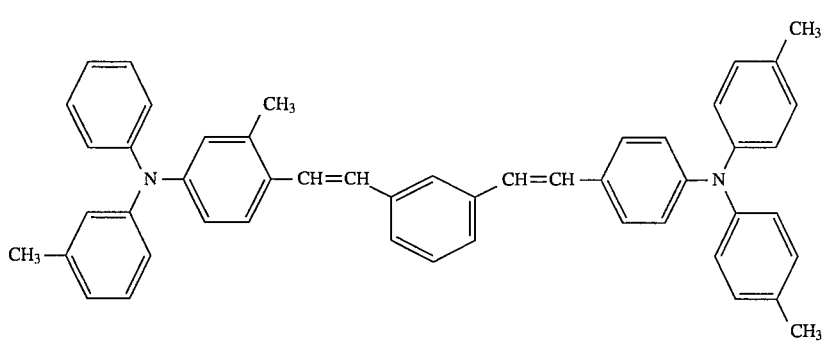
(VII-77)
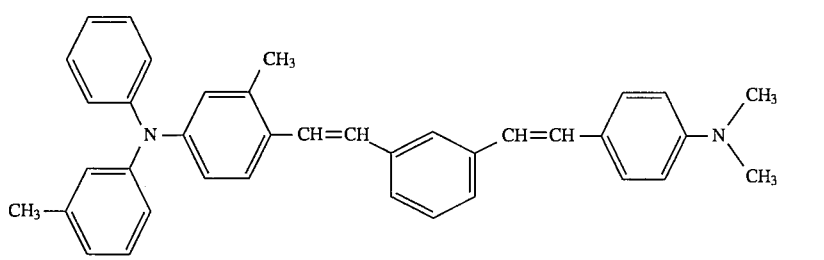
(VII-78)
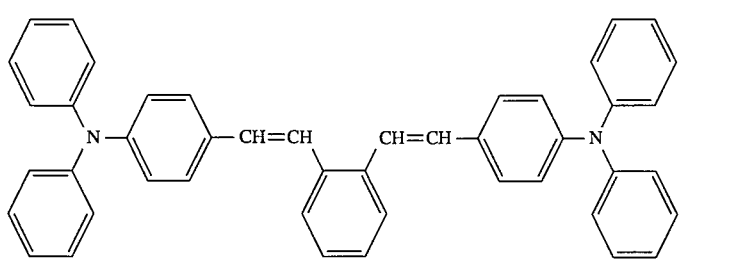
(VII-79)

-continued
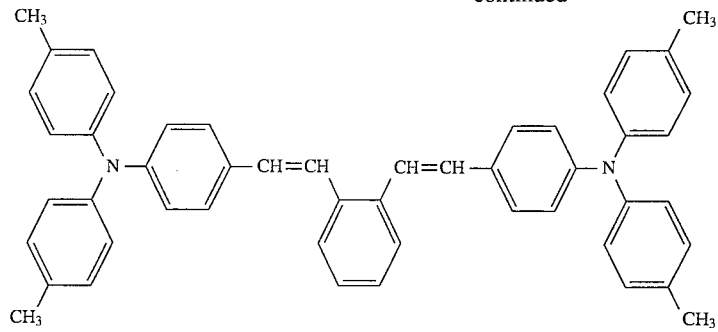
(VII-80)
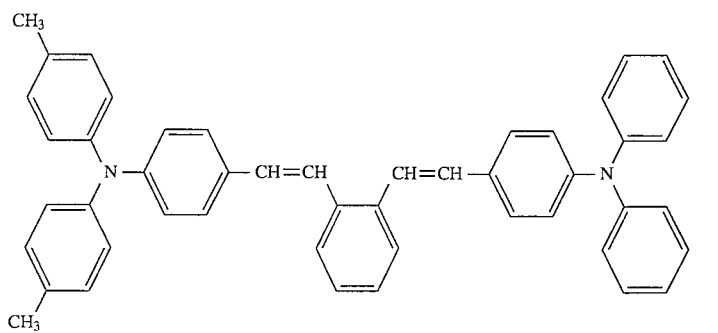
(VII-81)
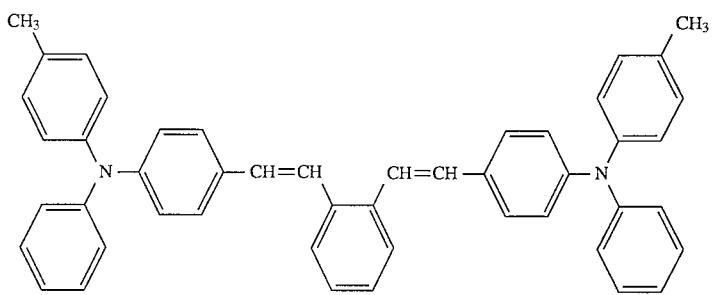
(VII-82)
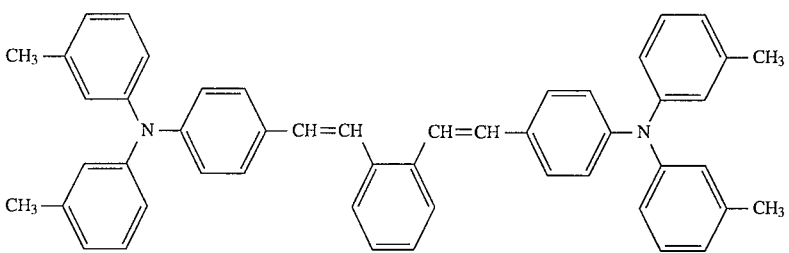
(VII-83)
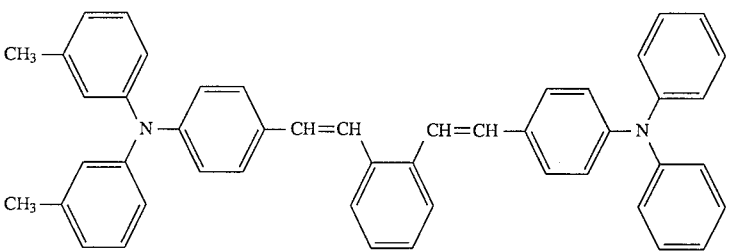
(VII-84)

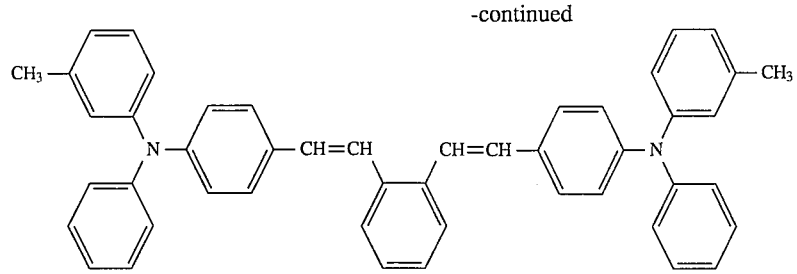
(VII-85)
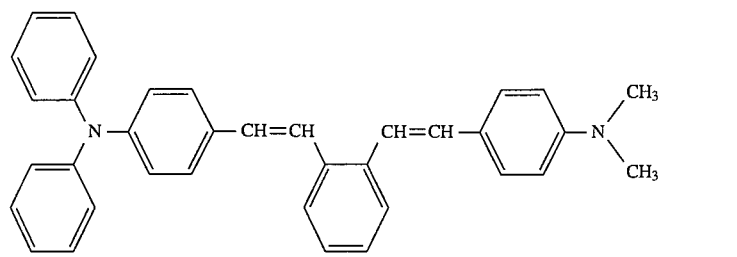
(VII-86)
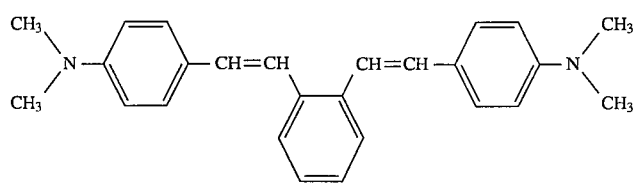
(VII-87)
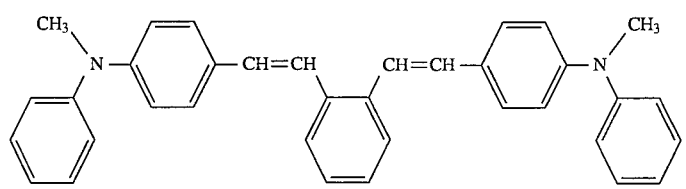
(VII-88)
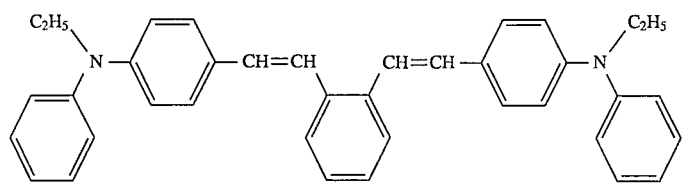
(VII-89)
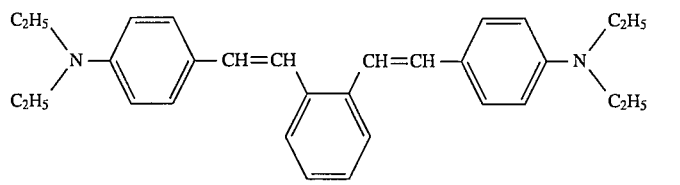
(VII-90)
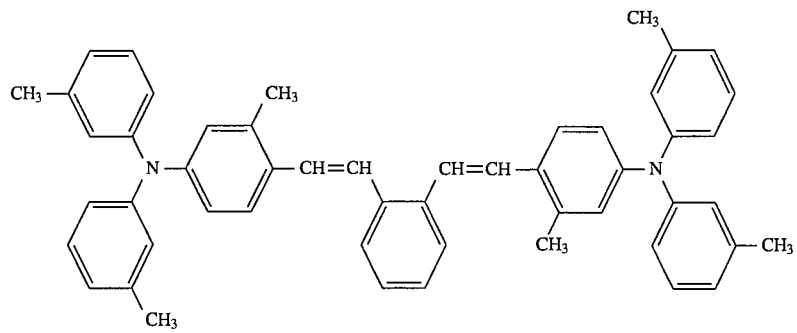
(VII-91)

-continued

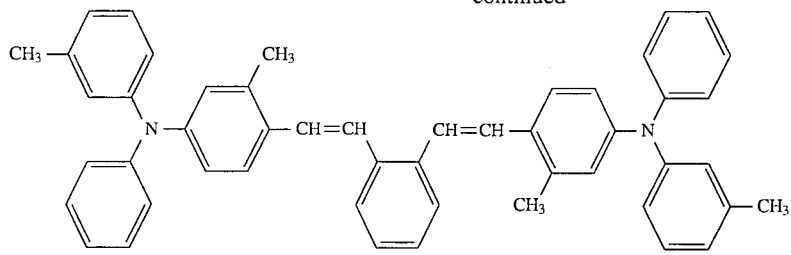
(VII-92)

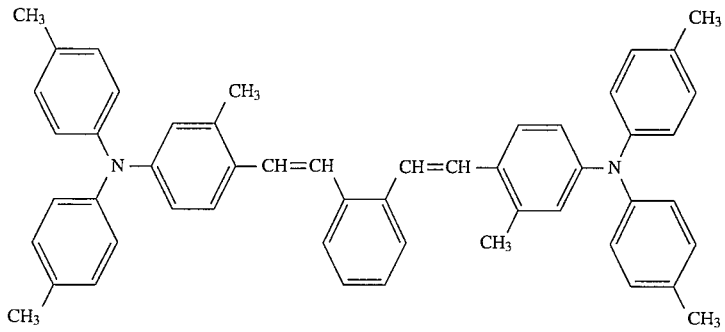
(VII-93)

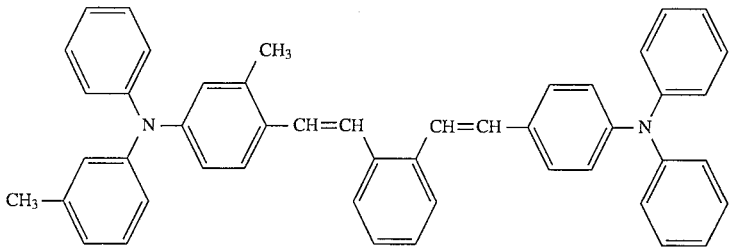
(VII-94)

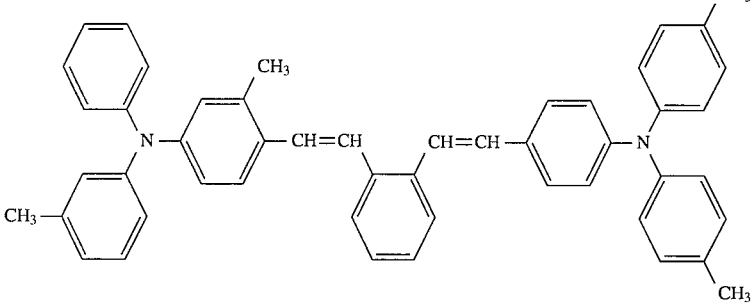
(VII-95)

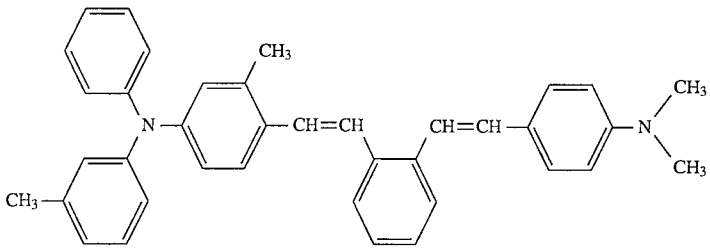
(VII-96)

However, the material responsible for transporting charge carriers is not limited to one o f the above compounds but also other materials which have been known in the art, for example hydrazone compounds described in the documents such as a specification of European Patent Application No. 13172, pyrazoline compounds described in Japanese Patent Application Laid-open No. 105536/1974, oxadiazole compounds described in Japanese Patent Application Laid-open No. 112637/1979 and U.S. Pat. No. 318,994, styryl compounds referenced in Japanese Patent Application Laid-open No. 3173/1975, arylamine compounds described in U.S. Pat. No. 3,567,450, Japanese Patent Application Publication No. 35702/197- 4, German Patent No. 1110518, U.S. Pat. Nos. 3,180,703, 3,240,597, 3,658,520, 4,232,103, 4,175,961, 4,012,376, Japanese Patent Application Laid-open No. 144250/1980, Japanese Patent Application Laid-open No. 119132/1981, and Japanese Patent Application Publication No. 27577/1964, oxazole compounds described in U.S. Pat. No. 3,543,546, pyrazoline and pyrazolone compounds described in U.S. Pat. No. 3,180,729 and Japanese Patent Application Laid-open No. 105536/1974, polyarylalkane compounds described in U.S. Pat. Nos. 3,615,402, 3,820, 989, 3,542,544, Japanese Patent Application Publication No. 555/1970, and Japanese Patent Application Publication No. 10983/1976, polyvinylcarbazole compounds and their derivatives described in Japanese Patent Application Publication No. 10966/1959, polymers of N-acrylamide methylcarbazole described in Japanese Patent Application Laid-open 85337/1975, 6-vinylindro-(2,3-6)-quinoxaline polymers described in Japanese Patent Application Laid-open 93432/1975, vinyl polymers described in Japanese Patent Application Publication No. 18674/1968 and Japanese Patent Application Publication No. 19192/1968, triphenylmethane polymers described in Japanese Patent Application Laid-open No. 90883/1981 and Japanese Patent Application Laid-open No. 161550/1981, styrerie copolymers described in Japanese Patent Application Publication No. 19193/1968, polyindene, polyacenaphthene, copolymers of styrene with acenaphthylene, and formaldehyde condensation resin described in Japanese Patent Application Publication No. 13940/1981. If these charge-carrier transport materials have the abilities of forming their films, they can be used in the form of aqueous solution and applied on a substrate to make a charge generation layer. In the case of low molecular weight compound which does not show the ability of forming its film, however, it may be solved in an aqueous solution with a resin having the ability of film-formation. In general, the thickness of charge transport layer is preferably in the range of 5 µm to 40 µm.

The above photosensitive layer 4 may be optionally comprised of an electron acceptor for the purpose of increasing photo sensitivity and preventing the decrease in residual potential, and the change in electrophotographic characteristics in repeat use. The material to be used as an electron acceptor can be selected from succinic anhydride, maleic anhydride, dibromosuccinic anhydride, phthalic anhydride, 3-nitrophtalic anhydride, 4-nitrophtalic anhydride, pyromellitic anhydride, pyromellitic acid, trimellitic acid, trimellitic anhydride, phthalimide, 4-nitrophthalimide, tetracyanoethylene, tetracyanoquinodimethane, chloranil, and bromanil, o-nitrobenzoic acid, and the like, which are characterized by their good electron affinities.

In the above photosensitive layer 4, furthermore, at least one of deterioration-preventing agents such as anti-oxidizing agents and light-stabilizing agents may be included for improving the stabilities thereof to harmful light and on the environmental conditions. The material to be used for attaining that purpose may be selected from chromanol derivatives such as tocopherol and their etherified compounds or esterified compounds, polyarylalkane compounds, hydroquinone derivatives and their mono-etherified compounds or di-esterified compounds, benzophenone derivatives, benzotriazole derivatives, thioetherified compounds, phenylene diamine derivatives, phosphonate, phosphite, phenol compounds, hindered phenol compound, straight-chain amine compounds, cyclic amine compounds, hindered amine compounds, and the like.

Each layer of the photoreceptor of the present invention can be formed by using the well-known device such as dip coater, spray coater, wire-bar coater, applicator, doctor blade, roller coater, curtain coater, and bead coater.

Preferable embodiments of the present invention will now be described in detail. However, the present invention is not to be restricted to these embodiments. In the embodiments, "parts" stands for "parts by weight" and "%" stands for "percent by weight or wt %".

EXAMPLE 1

An aluminum-alloy in the shape of a cylinder with 60 mm in outer diameter, 348 mm in length, and 1 mm in thickness was provided as a conductive substrate. An intermediate layer of 0.5 mm in thickness was formed by covering an outer peripheral surface of the conductive substrate with a soluble polyamide resin (Daiamid T-171, manufactured by DAICEL-HÜLS LTD.). Then a charge generation layer of 0.2 mm in thickness was formed on the intermediate layer by immersing in a coating solution. The coating solution for the charge generation layer was prepared by dispersing 2.1 parts of bisazo compound represented by the following formula A-1, 1.0 part of polyvinylacetal (SLEC KS-1, manufactured by Sekisui Chemical Industries, Co., LTD.), 16 parts of methylethylketon, and 9 parts of cyclohexan with each other by a sand mill, followed by adding 75 parts of methylethylketone.

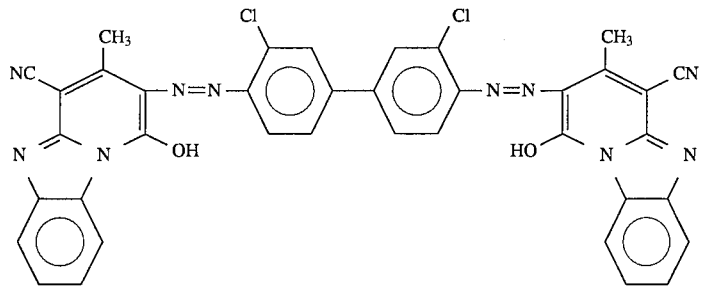

(A-1)

After that, a polycarbonate resin (Iupilon PCZ-300, manufactured by Mitsubishi Gas Chemicals, Co., LTD.) and a charge transport material represented by the following formula B-1 are mixed together at the ratio of 1:1. Then the above compound I-1 was added into the mixture. By repeating the same steps, the mixtures containing 5%, 10%, and 15% of the compound I-1 were obtained, respectively. Furthermore, each mixture was dissolved in a solution of tetrahydrofuran (hereinafter, referred as THF) to obtain 20% solution thereof. Consequently, 20% solutions containing 5%, 10%, and 15% of the compound I-1 were prepared, respectively, as coating solutions for forming the charge transport layer. Each coating solution was applied on a surface of the above charge generation layer by means of dip coating and then dried to form a charge generation layer of 35 mm in thick, resulting that the photoreceptors of Examples I-1, I-2, and I-3 were obtained, respectively.

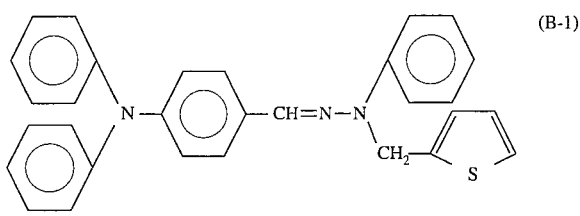

(B-1)

For making the comparison, a photoreceptor of Comparative example I-1 was prepared by forming a charge transport layer by the same way as that of the above examples except that the coating solution without the above compound I-1 was used.

The electrophotographic properties of the each photoreceptor was evaluated by utilizing an electrical drum analyzer (Model EPA-8100, manufactured by Kawaguchi Denki Seisakusyo). That is, the photoreceptor was placed in the device as a sample. The sample was charged by using a corotoron at −800 V under the condition of rotating the sample at a peripheral speed of 60 mm/sec. After the step of charging, the photoreceptor was left in dark for 5 seconds to evaluate the rate of lowering a surface potential of the photoreceptor (hereinafter, referred as a dark-decay rate $V_{k5}$ (%) of the photoreceptor). The photoreceptor was further subjected to light (2 lux) illuminated by a halogen lamp at the wavelengths of under 650 nm. The time required for the irradiation to decrease the surface potential of the photoreceptor to −400 V (i.e., a half of the charged potential) was measured and the amount of the irradiation $E_{1/2}$ (lux·sec) was calculated to estimate the photo-sensitivities of the sample. The above evaluation was performed before and after leaving the sample in the ozonized atmosphere (i.e., 1,000 ppm of ozone) to evaluate the deterioration of the photoreceptor. The results were listed in Table 1.

because of the marked variations in the dark-decay ratio $V_{k5}$ and the light efficiency $E_{1/2}$. Consequently, the above compound I-1 was very effective to obtain excellent electrophotographic properties of the photoreceptor.

EXAMPLE 2

Photoreceptors of Examples 2-1, 2-2, and 2-3 were prepared by the same way as that of Example 1, excepting that the present example used a charge transport material represented by the formula (B-2) below. For making the comparison, a photoreceptor of Comparative example 2-1 was prepared without using the above compound I-1.

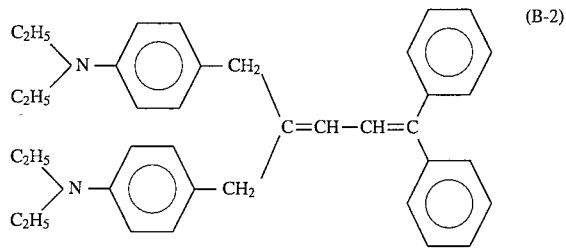

(B-2)

The obtained photoreceptors were subjected to the same evaluation test as that of Example 1 and the results were listed in Table 2.

TABLE 1

| Examples | Aditive added in charge transport layer (%) | Electrophotographic characteristics | | | |
|---|---|---|---|---|---|
| | | at beggining | | after leave in ozone | |
| | | $V_{k5}$ (V) | $E_{1/2}$ (lux · sec) | $V_{k5}$ (V) | $E_{1/2}$ (lux · sec) |
| Example 1-1 | Compound (1-1) 5% | 95 | 0.7 | 90 | 0.8 |
| Example 1-2 | Compound (1-1) 10% | 94 | 0.7 | 91 | 0.8 |
| Example 1-3 | Compound (1-1) 15% | 93 | 0.8 | 92 | 0.8 |
| Comparative example 1-1 | non | 96 | 0.8 | 82 | 1.5 |

As shown in Table 1, comparing with the samples of Examples I-1, I-2, and I-3, the photoreceptor of Comparative example I-1 show poor electrophotographic characteristics

TABLE 2

| Examples | Aditive added in charge transport layer (%) | Electrophotographic characteristics | | | |
|---|---|---|---|---|---|
| | | at beggining | | after leave in ozone | |
| | | $V_{k5}$ (V) | $E_{1/2}$ (lux · sec) | $V_{k5}$ (V) | $E_{1/2}$ (lux · sec) |
| Example 2-1 | Compound (1-1) 5% | 96 | 1.1 | 92 | 1.2 |
| Example 3-2 | Compound (1-1) 10% | 96 | 1.2 | 93 | 1.2 |
| Example 2-3 | Compound (1-1) 15% | 95 | 1.1 | 91 | 1.1 |
| Comparative example 2-1 | non | 98 | 1.0 | 89 | 3.0 |

As shown in Table 2, comparing with the samples of Examples 2-1, 2-2, and 2-3, the photoreceptor of Comparative example 2-1 show poor electrophotographic characteristics because of the marked variations in the dark-decay ratio $V_{k5}$ and the light efficiency $E_{1/2}$. Consequently, the above compound I-1 was very effective to obtain excellent electrophotographic properties of the photoreceptor.

EXAMPLE 3

In this example, photoreceptors of Example 3-1, 3-2, and 3-3 were prepared by the same way as that of Example 1, excepting the charge generation material and the charge transport material. In this example, a bis-azo compound represented by the formula A-2 below was used as a charge generation material and a mixture of a compound represented by the formula B-3 below and a compound represented by the formula B-4 at the ratio of 1:1. In stead of the compound of the formula I-1, in addition, a compound represented by the formula I-2 was added in the charge transport layer. Furthermore, the samples was prepared so as to include 3%, 6%, and 9% of the additive in the charge transport layer. For making the comparison, a photoreceptor of Comparative example 3-1 having a charge transport layer without including the compound I-2 was prepared.

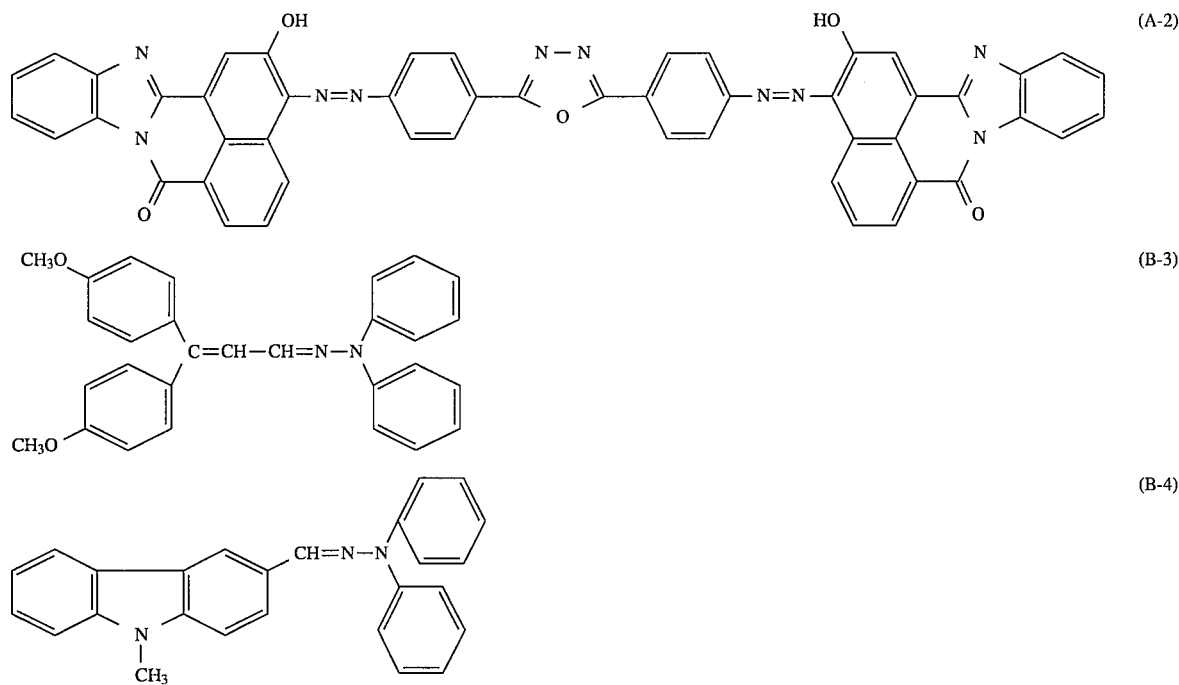

The obtained photoreceptors were subjected to the same evaluation test as that of Example 1 to estimate their electrophotographic properties and whether they were deteriorated by the ozone or not. The results were listed in Table 3.

TABLE 3

| Examples | Aditive added in charge transport layer (%) | Electrophotographic characteristics | | | |
|---|---|---|---|---|---|
| | | at beggining | | after leave in ozone | |
| | | $V_{k5}$ (V) | $E_{1/2}$ (lux · sec) | $V_{k5}$ (V) | $E_{1/2}$ (lux · sec) |
| Example 3-1 | Compound (1-2) 3% | 97 | 1.0 | 92 | 1.1 |
| Example 3-2 | Compound (1-2) 6% | 97 | 1.1 | 91 | 1.4 |
| Example 3-3 | Compound (1-3) 9% | 96 | 1.1 | 90 | 1.1 |
| Comparative example 3-1 | non | 98 | 0.9 | 84 | 2.8 |

As shown in Table 3, comparing with the samples of Examples 3-1, 3-2, and 3-3, the photoreceptor of Comparative example 3-1 show poor electrophotographic characteristics because of the marked variations in the dark-decay ratio $V_{k5}$ and the light efficiency $E_{1/2}$. Consequently, the above compound I-2 was very effective to obtain excellent electrophotographic properties of the photoreceptor.

EXAMPLE 4

In this example, photoreceptors of Example 4-1 and 4-2 were prepared by the same way as that of Example 3, excepting the charge transport material. In this example, the compounds represented by the formulae 1-3 and I-4 were used as additives of the charge transport layer. In addition, each sample was prepared so as to include 6% of the additive in the charge transport layer. For making the comparison, a photoreceptor of Comparative example 4-1 having a charge transport layer without including the above compounds was prepared.

The obtained photoreceptors were subjected to the same evaluation test as that of Example 1 to estimate their electrophotographic properties and whether they were deteriorated by the ozone or not. The results were listed in Table 4.

As shown in Table 4, comparing with the samples of Examples 4-1 and 4-2, the photoreceptor of Comparative example 4-1 showed poor electrophotographic characteristics because of the marked variations in the dark-decay ratio $V_{k5}$ and the light efficiency $E_{1/2}$. Consequently, the above compound I-2 was very effective to obtain excellent electrophotographic properties of the photoreceptor.

EXAMPLE 5

Photoreceptors of Examples 5-1, 5-2, and 5-3 were prepared by the same way as that of Example 1, excepting the followings. In this example, that is, the above compound II-1 was used as an additive of the charge transport layer with the amount of 2%, 4%, or 6%. For making the comparison, a photoreceptor of Comparative example was prepared without adding the above compound II-1 in the charge transport layer.

The obtained photoreceptors were evaluated by the same way as that of Example 1 and the rests were listed in Table 5.

TABLE 4

| Examples | Aditive added in charge transport layer (%) | Electrophotographic characteristics | | | |
|---|---|---|---|---|---|
| | | at beggining | | after leave in ozone | |
| | | $V_{k5}$ (V) | $E_{1/2}$ (lux · sec) | $V_{k5}$ (V) | $E_{1/2}$ (lux · sec) |
| Example 4-1 | Compound (1-3) 6% | 96 | 1.2 | 90 | 1.4 |
| Example 4-2 | Compound (1-4) 6% | 95 | 1.4 | 91 | 1.5 |
| Comparative example 4-1 | non | 98 | 0.9 | 84 | 2.8 |

TABLE 5

| Examples | Aditive added in charge transport layer (%) | Electrophotographic characteristics | | | |
|---|---|---|---|---|---|
| | | at beggining | | after leave in ozone | |
| | | $V_{k5}$ (V) | $E_{1/2}$ (lux · sec) | $V_{k5}$ (V) | $E_{1/2}$ (lux · sec) |
| Example 5-1 | Compound (II-1) 2% | 94 | 0.7 | 92 | 0.8 |
| Example 5-2 | Compound (II-1) 4% | 93 | 0.7 | 92 | 0.8 |
| Example 5-3 | Compound (II-1) 6% | 91 | 0.8 | 91 | 0.8 |
| Comparative example 1-1 | non | 96 | 0.8 | 82 | 1.5 |

As shown in Table 5, comparing with the samples of Examples 5-1, 5-3, and 5-3, the photoreceptor of Comparative example 5-1 showed poor electrophotographic characteristics because of the marked variations in the dark-decay ratio $V_{k5}$ and the light efficiency $E_{1/2}$. Consequently, the above compound II-1 was very effective to obtain excellent electrophotographic properties of the photoreceptor.

TABLE 7

| Examples | Aditive added in charge transport layer (%) | Electrophotographic characteristics | | | |
|---|---|---|---|---|---|
| | | at beggining | | after leave in ozone | |
| | | $V_{k5}$ (V) | $E_{1/2}$ (lux · sec) | $V_{k5}$ (V) | $E_{1/2}$ (lux · sec) |
| Example 7-1 | Compound (II-2) 3% | 97 | 1.1 | 92 | 1.2 |
| Example 7-2 | Compound (II-2) 6% | 93 | 1.2 | 90 | 1.4 |
| Example 7-3 | Compound (II-2) 9% | 91 | 1.4 | 90 | 1.5 |
| Comparative example 7-1 | non | 98 | 0.9 | 84 | 2.8 |

EXAMPLE 6

Photoreceptors of Examples 6-1, 6-2, and 6-3 were prepared by the same way as that of Example 2, eccepting the followings. In this example, that is, the above compound II-1 was used as an additive of the charge transport layer with the amount of 2%, 4%, or 6%. For making the comparison, a photoreceptor of Comparative example was prepared without adding the above compound II-1 in the charge transport layer.

The obtained photoreceptors were evaluated by the same way as that of Example 1 and the rests were listed in Table 6.

TABLE 6

| Examples | Aditive added in charge transport layer (%) | Electrophotographic characteristics | | | |
|---|---|---|---|---|---|
| | | at beggining | | after leave in ozone | |
| | | $V_{k5}$ (V) | $E_{1/2}$ (lux · sec) | $V_{k5}$ (V) | $E_{1/2}$ (lux · sec) |
| Example 6-1 | Compound (II-1) 2% | 95 | 1.1 | 92 | 1.2 |
| Example 6-2 | Compound (II-1) 4% | 94 | 1.1 | 93 | 1.2 |
| Example 6-3 | Compound (II-1) 6% | 93 | 1.1 | 91 | 1.1 |
| Comparative example 6-1 | non | 98 | 1.1 | 89 | 3.0 |

As shown in Table 6, comparing with the samples of Examples 6-1, 6-2, and 6-3, the photoreceptor of Comparative example 6-1 showed poor electrophotographic characteristics because of the marked variations in the dark-decay ratio $V_{k5}$ and the light efficiency $E_{1/2}$. Consequently, the above compound II-1 was very effective to obtain excellent electrophotographic properties of the photoreceptor.

EXAMPLE 7

Photoreceptors of Examples 7-1, 7-2, and 7-3 were prepared by the same way as that of Example 3, eccepting the followings. In this example, that is, the above compound II-2 was used as an additive of the charge transport layer. For making the comparison, a photoreceptor of Comparative example 7-2 was prepared without adding the above compound II-2 in the charge transport layer.

The obtained photoreceptors were evaluated by the same way as that of Example 1 and the rests were listed in Table 7.

As shown in Table 7, comparing with the samples of Examples 7-1, 7-2, and 7-3, the photoreceptor of Comparative example 7-1 showed poor electrophotographic characteristics because of the marked variations in the dark-decay ratio $V_{k5}$ and the light efficiency $E_{1/2}$. Consequently, the above compound II-2 was very effective to obtain excellent electrophotographic properties of the photoreceptor.

EXAMPLE 8

Photoreceptors of Examples 8-1, 8-2, and 8-3 were prepared by the same way as that of Example 7, eccepting the followings. In this example, that is, the above compounds II-3, II-4, II-5, and II-6 were used instead of the additive of the charge transport layer of Example 7. In addition, the amount of the additive with respect to the charge transport layer is 6%. For making the comparison, a photoreceptor of Comparative example 8-1 was prepared without adding the above compounds in the charge transport layer.

The obtained photoreceptors were evaluated by the same way as that of Example 1 to estimate their electrophotographic properties and their deterioration under the ozone. The results were listed in Table 8.

teristics because of the marked variations in the dark-decay ratio $V_{k5}$ and the light efficiency $E_{1/2}$. Consequently, the above compound III-1 was very effective to obtain excellent electrophotographic properties of the photoreceptor.

TABLE 8

| Examples | Aditive added in charge transport layer (%) | Electrophotographic characteristics | | | |
|---|---|---|---|---|---|
| | | at beggining | | after leave in ozone | |
| | | $V_{k5}$ (V) | $E_{1/2}$ (lux · sec) | $V_{k5}$ (V) | $E_{1/2}$ (lux · sec) |
| Example 8-1 | Compound (II-3) 6% | 96 | 1.2 | 90 | 1.4 |
| Example 8-2 | Compound (II-4) 6% | 95 | 1.4 | 91 | 1.5 |
| Example 8-3 | Compound (II-5) 6% | 97 | 1.4 | 92 | 1.4 |
| Example 8-4 | Compound (II-6) 6% | 94 | 1.3 | 91 | 1.4 |
| Comparative example 8-1 | non | 98 | 0.9 | 84 | 2.8 |

As shown in Table 8, comparing with the samples of Examples 6-1, 6-2, and 6-3, the photoreceptor of Comparative example 6-1 showed poor electrophotographic characteristics because of the marked variations in the dark-decay ratio $V_{k5}$ and the light efficiency $E_{1/2}$. Consequently, the above compounds II-3, II-4, II-5, and II-6 were very effective to obtain excellent electrophotographic properties of the photoreceptor.

EXAMPLE 9

Photoreceptors of Examples 9-1, 9-2, and 9-3 were prepared by the same way as that of Example 1, excepting the followings. In this example, that is, the above compound III-1 was used instead of the additive of the charge transport layer of Example 7. For making the comparison, a photoreceptor of Comparative example 10-1 was prepared without adding the above compound III-1 in the charge transport layer.

The obtained photoreceptors were evaluated by the same way as that of Example 1 to estimate their electrophotographic properties and their deterioration under the ozone. The results were listed in Table 9.

EXAMPLE 10

Photoreceptors of Examples 10-1, 10-2, and 10-3 were prepared by the same way as that of Example 2, excepting the followings. In this example, that is, the above compound III-1 was used instead of the additive of the charge transport layer of Example 2. For making the comparison, a photoreceptor of Comparative example 10-1 was prepared without adding the above compound III-1 in the charge transport layer.

The obtained photoreceptors were evaluated by the same way as that of Example 1 to estimate their electrophotographic properties and their deterioration under the ozone. The results were listed in Table 10.

TABLE 9

| Examples | Aditive added in charge transport layer (%) | Electrophotographic characteristics | | | |
|---|---|---|---|---|---|
| | | at beggining | | after leave in ozone | |
| | | $V_{k5}$ (V) | $E_{1/2}$ (lux · sec) | $V_{k5}$ (V) | $E_{1/2}$ (lux · sec) |
| Example 9-1 | Compound (III-1) 5% | 95 | 0.8 | 90 | 0.8 |
| Example 9-2 | Compound (III-1) 10% | 95 | 0.7 | 91 | 0.8 |
| Example 9-3 | Compound (III-1) 15% | 93 | 0.8 | 92 | 0.8 |
| Comparative example 7-1 | non | 96 | 0.8 | 82 | 1.5 |

As shown in Table 9, comparing with the samples of Examples 9-1, 9-2, and 9-3, the photoreceptor of Comparative example 9-1 showed poor electrophotographic charac-

TABLE 10

| Examples | Aditive added in charge transport layer (%) | Electrophotographic characteristics | | | |
|---|---|---|---|---|---|
| | | at beggining | | after leave in ozone | |
| | | $V_{k5}$ (V) | $E_{1/2}$ (lux · sec) | $V_{k5}$ (V) | $E_{1/2}$ (lux · sec) |
| Example 10-1 | Compound (III-1) 5% | 96 | 1.2 | 92 | 1.2 |
| Example 10-2 | Compound (III-2) 10% | 97 | 1.2 | 93 | 1.2 |
| Example 10-3 | Compound (III-2) 15% | 95 | 1.1 | 91 | 1.1 |
| Comparative example 10-1 | non | 98 | 1.0 | 89 | 3.0 |

As shown in Table 10, comparing with the samples of Examples 10-1, 10-2, and 10-3, the photoreceptor of Comparative example 9-1 showed poor electrophotographic characteristics because of the marked variations in the dark-decay ratio $V_{k5}$ and the amount of the irradiation $E_{1/2}$. Consequently, the above compound III-1 was very effective to obtain excellent electrophotographic properties of the photoreceptor.

EXAMPLE 11

Photoreceptors of Examples 11-1, 11-2, and 11-3 were prepared by the same way as that of Example 3, excepting the followings. In this example, that is, the above compound III-2 was used instead of the additive of the charge transport layer of Example 3. For making the comparison, a photoreceptor of Comparative example 11-1 was prepared without adding the above compound III-2 in the charge transport layer.

The obtained photoreceptors were evaluated by the same way as that of Example 1 to estimate their electrophotographic properties and their deterioration under the ozone. The results were listed in Table 11.

characteristics because of the marked variations in the dark-decay ratio $V_{k5}$ and the light efficiency $E_{1/2}$. Consequently, the above compound III-2 was very effective to obtain excellent electrophotographic properties of the photoreceptor.

EXAMPLE 12

Photoreceptors of Examples 12-1, 12-2, and 12-3 were prepared by the same way as that of Example 11, excepting the followings. In this example, that is, the above compounds III-3, III-4, III-5, and III-6 were used instead of the additive of the charge transport layer of Example 11. For making the comparison, a photoreceptor of Comparative example 12-1 was prepared without adding the above compounds in the charge transport layer.

The obtained photoreceptors were evaluated by the same way as that of Example 1 to estimate their electrophotographic properties and their deterioration under the ozone. The results were listed in Table 12.

TABLE 11

| Examples | Aditive added in charge transport layer (%) | Electrophotographic characteristics | | | |
|---|---|---|---|---|---|
| | | at beggining | | after leave in ozone | |
| | | $V_{k5}$ (V) | $E_{1/2}$ (lux · sec) | $V_{k5}$ (V) | $E_{1/2}$ (lux · sec) |
| Example 11-1 | Compound (III-2) 3% | 97 | 1.0 | 92 | 1.1 |
| Example 11-2 | Compound (III-2) 6% | 97 | 1.1 | 91 | 1.3 |
| Example 11-3 | Compound (III-2) 9% | 97 | 1.1 | 91 | 1.2 |
| Comparative example 7-1 | non | 98 | 0.9 | 84 | 2.8 |

As shown in Table 11, comparing with the samples of Examples 11-1, 11-2, and 11-3, the photoreceptor of Comparative example 11-1 showed poor electrophotographic

TABLE 12

| Examples | Aditive added in charge transport layer (%) | Electrophotographic characteristics | | | |
|---|---|---|---|---|---|
| | | at beggining | | after leave in ozone | |
| | | $V_{k5}$ (V) | $E_{1/2}$ (lux · sec) | $V_{k5}$ (V) | $E_{1/2}$ (lux · sec) |
| Example 12-1 | Compound (III-3) 6% | 96 | 1.2 | 90 | 1.4 |
| Example 12-2 | Compound (III-4) 6% | 95 | 1.4 | 91 | 1.5 |
| Example 12-3 | Compound (III-5) 6% | 96 | 1.5 | 91 | 1.6 |
| Example 12-4 | Compound (III-6) 6% | 96 | 1.5 | 92 | 1.7 |
| Comparative example 12-1 | non | 98 | 0.9 | 84 | 2.8 |

As shown in Table 12, comparing with the samples of Examples 12-1, 12-2, and 12-3, the photoreceptor of Comparative example 12-1 showed poor electrophotographic characteristics because of the marked variations in the dark-decay ratio $V_{k5}$ and the the light efficiency $E_{1/2}$. Consequently, the above compounds III-3, III-4, III-5, and III-6 were very effective to obtain excellent electrophotographic properties of the photoreceptor.

EXAMPLE 13

A coating solution for charge-generation layer was prepared by the steps of:

dispersing 2.1 parts of bis-azo compound represented by the formula A-1 as a charge generation material; 1.0 part of polyvinyl acetal (SLEC KS-1, manufactured by Sekisui Chemical Industries, Co., LTD.); and 1.0 parts of methylethylketone; and 9 parts of cyclohexane by using a sand mill to obtain a mixture; and further adding 75 parts of methylethylketone.

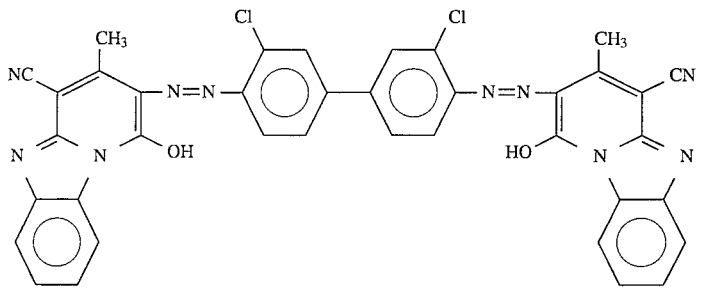
(A-1)

The obtained solution was applied on an outer peripheral surface of a cylinder (60 mm in outer diameter, 348 mm in length, and 1 mm in thickness) made of an aluminum alloy. In this case, the cylinder was previously covered with a film of solve polyamide resin film of 0.5 mm in thickness by means of dip-coating and then dried.

A solution for charge transport layer was prepared by the steps of:

blending a polycarbonate resin (Iupilon PCZ-300, manufactured by Mitsubishi Gas Chemicals, Co., LTD.) and the charge transport material represented by the formula B-1 at the ratio of 1:1 to obtain a mixture; adding the above compound IV-1 into the mixture so as to measure up to 3% with respect to the charge transport layer to be formed; and dissolving the mixture into THF to prepare three different 20% solutions.

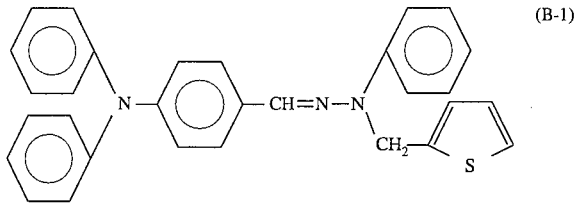
(B-1)

The obtained solution for charge transport layer was applied on a surface of the charge generation layer by means of dip-coating and then dried to obtain a charge transport layer of 35 mm in thickness. Consequently, a photoreceptor of Example 13-1 was prepared.

Furthermore, the above steps were repeated to obtain other photoreceptors, excepting the amount of the compound IV-1 in the above mixture. That is, photoreceptors of Examples 13-2 and 3-3 were prepared by adding the above compound IV-1 into the mixture so as to measure up to 5% and 7%, respectively.

For making the comparison, furthermore, a photoreceptor of Comparative example 13-1 was prepared by the same steps described above, excepting the charge transport layer. In this embodiment, that is, the charge transport layer was prepared by applying a solution without containing the above compound IV-1.

The electrophotographic properties of the each photoreceptor was evaluated by using a process-examination device for photoreceptors. That is, the photoreceptor was placed in the device as a sample. The sample was charged by using a corotoron at −800 V under the condition of rotating the sample at a peripheral speed of 60 mm/sec. After the step of charging, the photoreceptor was left in dark for 5 seconds to evaluate the rate of lowering a surface potential of the photoreceptor (hereinafter, referred as a dark-decay rate $V_{k5}$ (%) of the photoreceptor). The photoreceptor was further subjected to light (2 lux) illuminated by a halogen lamp at the wavelengths of under 650 nm. The time required for the exposure to decrease the surface potential of the photoreceptor to −400 V (i.e., a half of the change potential) was measured and the amount of the exposure $E_{1/2}$ (lux·sec) was calculated to estimate the photo-sensitivities of the sample. The above evaluation was preformed before and after leaving the sample in the ozonized atmosphere (i.e., 1,000 ppm of ozone) to evaluate the deterioration of the photoreceptor. The results were listed in Table 13.

TABLE 13

| Examples | Aditive added in charge transport layer (%) | Electrophotographic characteristics | | | |
|---|---|---|---|---|---|
| | | at beggining | | after leave in ozone | |
| | | $V_{k5}$ (V) | $E_{1/2}$ (lux · sec) | $V_{k5}$ (V) | $E_{1/2}$ (lux · sec) |
| Example 13-1 | Compound (IV-1) 3% | 93 | 0.6 | 92 | 0.8 |
| Example 13-2 | Compound (IV-1) 5% | 92 | 0.5 | 92 | 0.8 |
| Example 13-3 | Compound (IV-1) 7% | 94 | 0.7 | 93 | 0.8 |
| Comparative example 13-1 | non | 96 | 0.8 | 82 | 1.5 |

As shown in Table 13, comparing with the samples of Examples 13-1, 13-2, and 13-3, the photoreceptor of Comparative example 13-1 showed poor electrophotographic characteristics because of the marked variations in th dark-decay ratio $V_{k5}$ and the amount of the exposure $E_{1/2}$. Consequently, the above compound IV-1 was very effective to obtain excellent electrophotographic properties of the photoreceptor.

EXAMPLE 14

Photoreceptors of Examples 14-1, 14-2, and 14-3 were prepared by the same way as that of Example 13, excepting the charge transport material represented by the formula (B-2) below. Furthermore, the samples was prepared so as to include 2%, 4% of the additive in the charge transport layer. For making the comparison, a photoreceptor of Comparative example 14-1 was prepared without adding the above compound IV-1 in the charge transport layer.

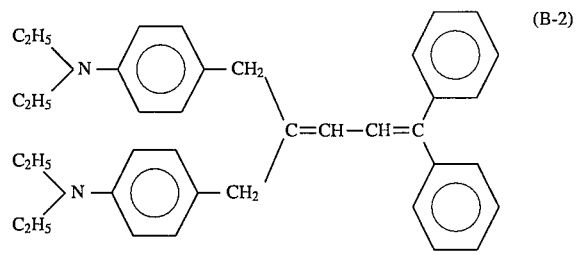
(B-2)

The obtained photoreceptors were evaluated by the same way as that of Example 13 to estimate their electrophotographic properties and their deterioration under the ozone. The results were listed in Table 14.

characteristics because of the marked variations in the dark-decay ratio $V_{k5}$ and the amount of the exposure $E_{1/2}$. Consequently, the above compound IV-1 was very effective to obtain excellent electrophotographic properties of the photoreceptor.

EXAMPLE 15

Photoreceptors of Examples 15-1, 15-2, and 15-3 were prepared by the same way as that of Example 13, excepting the followings. In this example, that is, a bis-azo compound A-2 represented by the formula below was used as a charge generation layer. In addition, a charge transport material was prepared by mixing compounds represented by the formula B-3 and B-4 at the ratio of 1:1. The mixture were added into a charge transport layer; adding the above compound IV-2 in to the change transport layer so as to measure up to the amount of 5%, 10%, or 20% with respect to the change transport layer. For making the comparison, a photoreceptor of Comparative example 15-1 was prepared without adding the above compound IV-2 in the charge tranport layer.

TABLE 14

| Examples | Aditive added in charge transport layer (%) | Electrophotographic characteristics | | | |
|---|---|---|---|---|---|
| | | at beggining | | after leave in ozone | |
| | | $V_{k5}$ (V) | $E_{1/2}$ (lux · sec) | $V_{k5}$ (V) | $E_{1/2}$ (lux · sec) |
| Example 14-1 | Compound (IV-1) 2% | 95 | 1.2 | 93 | 1.4 |
| Example 14-2 | Compound (IV-1) 4% | 92 | 1.4 | 90 | 1.5 |
| Example 14-3 | Compound (IV-1) 6% | 91 | 1.5 | 91 | 1.4 |
| Comparative example 14-1 | non | 98 | 1.0 | 80 | 3.0 |

As shown in Table 14, comparing with the samples of Examples 14-1, 14-2, and 14-3, the photoreceptor of Comparative example V4-1 showed poor electrophotographic

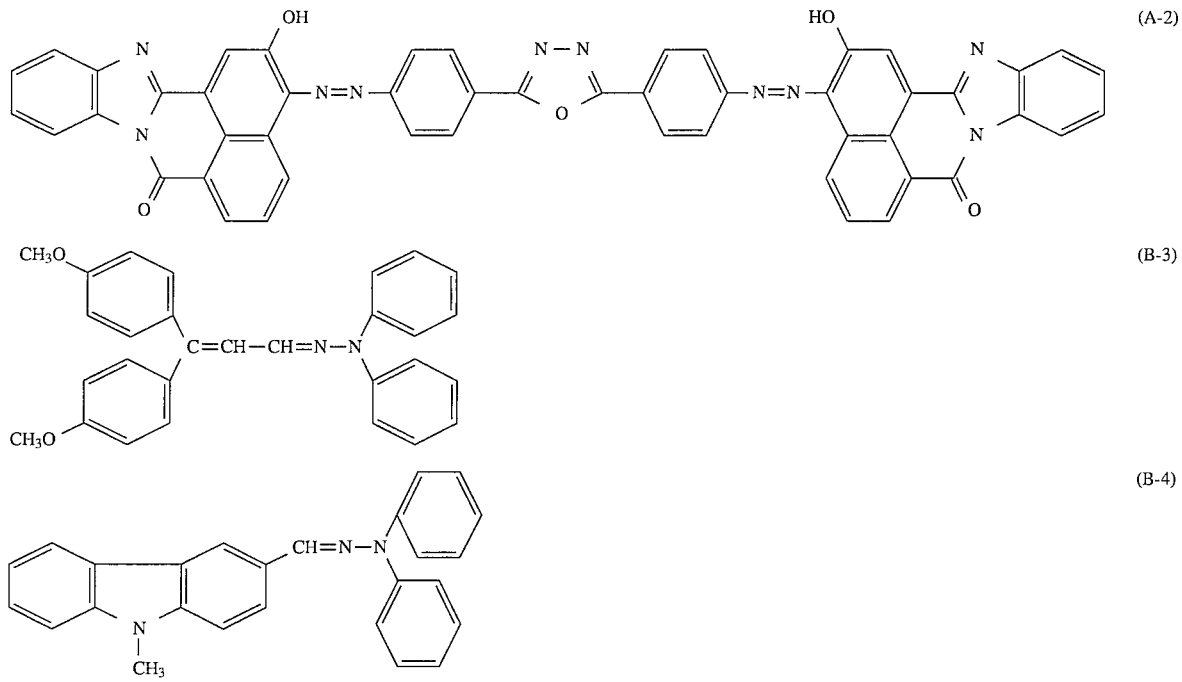

The obtained photoreceptors were evaluated by the same way as that of Example 13 to estimate their electrophotographic properties and their deterioration under the ozone. The results were listed in Table 15.

TABLE 15

| Examples | Aditive added in charge transport layer (%) | Electrophotographic characteristics | | | |
|---|---|---|---|---|---|
| | | at beggining | | after leave in ozone | |
| | | $V_{k5}$ (V) | $E_{1/2}$ (lux · sec) | $V_{k5}$ (V) | $E_{1/2}$ (lux · sec) |
| Example 15-1 | Compound (IV-2) 5% | 97 | 1.1 | 92 | 1.0 |
| Example 15-2 | Compound (IV-2) 10% | 93 | 1.2 | 90 | 1.3 |
| Example 15-3 | Compound (IV-2) 20% | 91 | 1.4 | 89 | 1.2 |
| Comparative example 15-1 | non | 98 | 0.9 | 80 | 3.1 |

As shown in Table 15, comparing with the samples of Examples 15-1, 15-2, and 15-3, the photoreceptor of Comparative example 15-1 showed poor electrophotographic characteristics because of the marked variations in the dark-decay ratio $V_{k5}$ and the amount of the exposure $E_{1/2}$. Consequently, the above compound IV-2 was very effective to obtain excellent electrophotographic properties of the photoreceptor.

EXAMPLE 16

Photoreceptors of Examples 16-1, 16-2, 16-3 and 16-4 were prepared by the same way as that of Example 15, excepting the followings. In this example, that is, the above compounds IV-3, IV-4, IV-5, or IV-6 was used as an additive of the charge transport layer with the amount of 10%. For making the comparison, a photoreceptor of Comparative example 16-1 was prepared without adding any of the above compound IV-7, IV-4, IV-5 or IV-6 in the charge transport layer.

The obtained photoreceptors were evaluated by the same way as that of Example 13 to estimate their electrophotographic properties and their deterioration under the ozone. The results were listed in Table 16.

dark-decay ratio $V_{k5}$ and the amount of the exposure $E_{1/2}$. Consequently, the above compound V-1 was very effective to obtain excellent electrophotographic properties of the photoreceptor.

TABLE 16

| Examples | Aditive added in charge transport layer (%) | Electrophotographic characteristics | | | |
|---|---|---|---|---|---|
| | | at beggining | | after leave in ozone | |
| | | $V_{k5}$ (V) | $E_{1/2}$ (lux · sec) | $V_{k5}$ (V) | $E_{1/2}$ (lux · sec) |
| Example 16-1 | Compound (IV-3) 10% | 96 | 1.1 | 93 | 1.0 |
| Example 16-2 | Compound (IV-4) 10% | 95 | 1.2 | 92 | 1.3 |
| Example 16-3 | Compound (IV-5) 10% | 97 | 1.3 | 90 | 1.1 |
| Example 16-4 | Compound (IV-6) 10% | 94 | 1.5 | 89 | 1.2 |
| Comparative example 16-1 | non | 98 | 0.9 | 80 | 2.8 |

As shown in Table 16, comparing with the samples of Examples 16-1, 16-2, 16-3 and 16-4 the photoreceptor of Comparative example 16-1 showed poor electrophotographic characteristics because of the marked variations in the dark-decay ratio $V_{k5}$ and the amount of the exposure $E_{1/2}$. Consequently, the above compounds IV-3 to IV-6 were very effective to obtain excellent electrophotographic properties of the photoreceptor.

EXAMPLE 17

Photoreceptors of Examples 17-1, 17-2, and 17-3 were prepared by the same way as that of Example 13, excepting the followings. In this example, that is, the above compound V-1 was used as an additive of the charge transport layer with the amount of 10%, 15%, or 20%. For making the comparison, a photoreceptor of Comparative example 17-1 was prepared without adding the above compound V-1 in the charge transport layer.

The obtained photoreceptors were evaluated by the same way as that of Example 13 to estimate their electrophotographic properties and their deterioration under the ozone. The results were listed in Table 17.

EXAMPLE 18

Photoreceptors of Examples 18-1, 18-2, and 18-3 were prepared by the same way as that of Example 13, excepting the followings. In this example, that is, the above compound V-1 was used as an additive of the charge transport layer with the amount of 10%, 15%, or 20%. For making the comparison, a photoreceptor of Comparative example 18-1 was prepared without adding the above compound V-1 in the charge transport layer.

The obtained photoreceptors were evaluated by the same way as that of Example 13 to estimate their electrophotographic properties and their deterioration under the ozone. The results were listed in Table 18.

TABLE 17

| Examples | Aditive added in charge transport layer (%) | Electrophotographic characteristics | | | |
|---|---|---|---|---|---|
| | | at beggining | | after leave in ozone | |
| | | $V_{k5}$ (V) | $E_{1/2}$ (lux · sec) | $V_{k5}$ (V) | $E_{1/2}$ (lux · sec) |
| Example 17-1 | Compound (V-1) 10% | 95 | 0.7 | 93 | 0.8 |
| Example 17-2 | Compound (V-1) 15% | 94 | 0.7 | 94 | 0.8 |
| Example 17-3 | Compound (V-1) 20% | 93 | 0.8 | 93 | 0.8 |
| Comparative example 17-1 | non | 96 | 0.8 | 82 | 2.0 |

As shown in Table 17, comparing with the samples of Examples 17-1, 17-2, and 17-3, the photoreceptor of Comparative example 17-1 showed poor electrophotographic characteristics because of the marked variations in the

TABLE 18

| Examples | Aditive added in charge transport layer (%) | Electrophotographic characteristics | | | |
|---|---|---|---|---|---|
| | | at beggining | | after leave in ozone | |
| | | $V_{k5}$ (V) | $E_{1/2}$ (lux · sec) | $V_{k5}$ (V) | $E_{1/2}$ (lux · sec) |
| Example 18-1 | Compound (V-1) 10% | 96 | 1.1 | 94 | 1.2 |
| Example 18-2 | Compound (V-1) 15% | 96 | 1.2 | 95 | 1.2 |
| Example 18-3 | Compound (V-1) 20% | 95 | 1.1 | 94 | 1.1 |
| Comparative example 18-1 | non | 98 | 1.0 | 89 | 3.0 |

As shown in Table 18, comparing with the samples of Examples 18-1, 18-2, and 18-3, the photoreceptor of Comparative example 18-1 showed poor electrophotographic characteristics because of the marked variations in the dark-decay ratio $V_{k5}$ and the amount of the exposure $E_{1/2}$. Consequently, the above compound V-1 was very effective to obtain excellent electrophotographic properties of the photoreceptor.

EXAMPLE 19

Photoreceptors of Examples 19-1, 19-2, and 19-3 were prepared by the same way as that of Example 15, excepting the followings. In this example, that is, the above compound V-2 was used as an additive of the charge transport layer with the amount of 5%, 10%, or 15%. For making the comparison, a photoreceptor of Comparative example 19-1 was prepared without adding the above compound V-2 in the charge transport layer.

The obtained photoreceptors were evaluated by the same way as that of Example 13 to estimate their electrophotographic properties and their deterioration under the ozone. The results were listed in Table 19.

characteristics because of the marked variations in the dark-decay ratio $V_{k5}$ and the amount of the exposure $E_{1/2}$. Consequently, the above compound V-2 was very effective to obtain excelent electrophotographic properties of the photoreceptor.

EXAMPLE 20

Photoreceptors of Examples 20-1, 20-2 20-3 and 20-4 were prepared by the same way as that of Example 19, excepting the followings. In this example, that is, the above compounds V-3, V-4, V-5, or V-6 was used as an additive of the charge transport layer with the amount of 10% thereof. For making the comparison, a photoreceptor of Comparative example 20-1 was prepared without adding any of the above compound V-3, V-4, V-5, V-6 in the charge transport layer.

The obtained photoreceptors were evaluated by the same way as that of Example 13 to estimate their electrophotographic properties and their deterioration under the ozone. The results were listed in Table 20.

TABLE 19

| Examples | Aditive added in charge transport layer (%) | Electrophotographic characteristics | | | |
|---|---|---|---|---|---|
| | | at beggining | | after leave in ozone | |
| | | $V_{k5}$ (V) | $E_{1/2}$ (lux · sec) | $V_{k5}$ (V) | $E_{1/2}$ (lux · sec) |
| Example 19-1 | Compound (V-2) 5% | 97 | 1.0 | 95 | 1.1 |
| Example 19-2 | Compound (V-2) 10% | 97 | 1.1 | 94 | 1.4 |
| Example 19-3 | Compound (V-2) 20% | 96 | 1.1 | 95 | 1.1 |
| Comparative example 19-1 | non | 98 | 0.9 | 84 | 2.8 |

As shown in Table 19, comparing with the samples of Examples 19-1, 19-2, and 19-3, the photoreceptor of Comparative example 19-1 showed poor electrophotographic

TABLE 20

| Examples | Aditive added in charge transport layer (%) | Electrophotographic characteristics | | | |
|---|---|---|---|---|---|
| | | at beggining | | after leave in ozone | |
| | | $V_{k5}$ (V) | $E_{1/2}$ (lux · sec) | $V_{k5}$ (V) | $E_{1/2}$ (lux · sec) |
| Example 20-1 | Compound (V-3) 10% | 96 | 1.2 | 93 | 1.4 |
| Example 20-2 | Compound (V-4) 10% | 95 | 1.4 | 94 | 1.5 |
| Example 20-3 | Compound (V-5) 10% | 96 | 1.5 | 93 | 1.6 |
| Example 20-4 | Compound (V-6) 10% | 96 | 1.5 | 95 | 1.5 |
| Comparative example 20-1 | non | 98 | 0.9 | 84 | 3.4 |

As shown in Table 20, comparing with the samples of Examples 20-1, 20-2, 20-3 and 20-4, the photoreceptor of Comparative example 20-1 showed poor electrophotographic characteristics because of the marked variations in the dark-decay ratio $V_{k5}$ and the amount of the exposure $E_{1/2}$. Consequently, the above compounds V-3 to V-6 were very effective to obtain excellent electrophotographic properties of the photoreceptor.

In the above examples, each electrophotographic photoreceptors used is in the type of laminating the charge transport layer on the charge generation layer. According to the present invention, however, the electrophotographic photoreceptor is not limited to that type. It is also possible to use the photoreceptor in the type of laminating the layers in reverse order, i.e., charge generation layer on the charge transport layer, and in the type that the photosensitive layer is formed as a single layered structure. In the laminated structure, one of the above chemical compounds represented by the formulae (I) to (V) is added in the charge transport layer but not limited to. It is also possible to add the compound in the charge generation layer. In the single layered structure, the above compound is distributed throughout the photosensitive layer.

In accordance with the present invention, consequently, the electrophotographic photoreceptor with a long life span, showing excellent electrophotographic characteristics and durability and maintains the stabilities of these characteristics in repeat use, can be obtained by incorporating one of the chemical compounds represented by the formulae (I) to (V).

What is claimed is:

1. An electrophotographic photoreceptor, comprising:
   a conductive substrate; and
   a photosensitive layer formed on said conductive substrate,
   wherein said photosensitive layer contains one compound selected from the group consisting of compounds respectively represented by formulae (I), (II), (III), (IV), and (V);

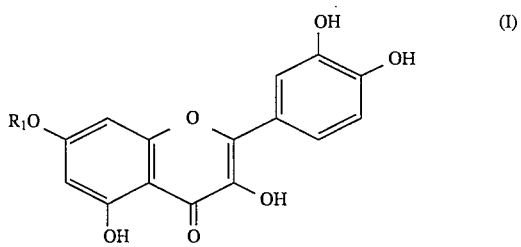

wherein $R_1$ stands for an atom or a group selected from the group consisting of a hydrogen atom, an alkyl group, an acyl group, and glycocyl group;

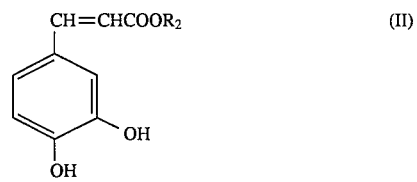

wherein $R_2$ stands for an atom or a group selected from the group consisting of a hydrogen atom, an alkyl group which may optionally have at least one substituent, and an aryl group which may optionally have at least one substituent;

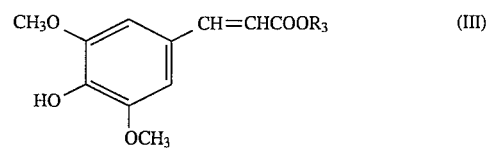

wherein $R_3$ stands for an atom or a group selected from the group consisting of a hydrogen atom, an alkyl group which may optionally have at least one substituent, and an aryl group which may optionally have at least one substituent;

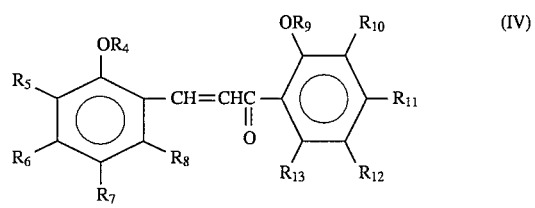

wherein each of $R_4$ to $R_{13}$ stands for an atom or a group selected from the group consisting of a hydrogen atom, an alkyl group which may optionally have at least one substituent, and an aryl group which may optionally have at least one substituent; and

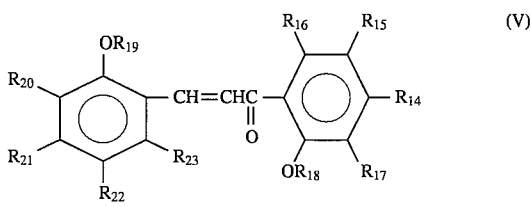

wherein each of $R_{14}$ to $R_{23}$ stands for an atom or a group selected from the group consisting of a hydrogen atom, an alkyl group, an alkoxy group, an aroyl group, and an aryl group, which may optionally have at least one substituent.

2. The electrophotographic photoreceptor as claimed in claim 1,
   wherein said one compound is present in an amount ranging from 0.1 to 30 percent by weight of said photosensitive layer.

3. The electrophotographic photoreceptor as claimed in claim 1,
   wherein said photosensitive layer has a single-layer structure and comprises a charge generation material and a charge transport material.

4. The electrophotographic photoreceptor as claimed in claim 1,
   wherein said photosensitive layer has a multi-layered structure having a charge generation layer comprising a charge generation material and a charge transport layer comprising a charge transport material.

5. The electrophotographic photoreceptor as claimed in claim 4,
   wherein said one compound is contained in said charge transport layer.

6. The electrophotographic photoreceptor as claimed in claim 1, further comprising an under-coating layer provided between said conductive substrate and said photosensitive layer.

7. The electrophotographic photoreceptor as claimed in claim 6,
   wherein said under-coating layer is a hardened film mainly comprising melamine resin, at least one of an aromatic carboxylic acid and an aromatic carboxylic anhydride, and iodine, which iodine is fixed within said hardened film.

8. The electrophotographic photoreceptor as claimed in claim 3, wherein said charge transport material is a hydrazone compound represented by formula (VI):

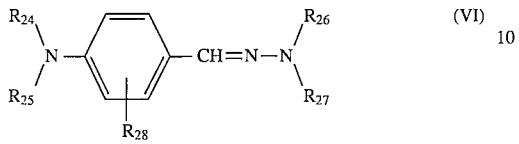

wherein each of $R_{24}$, $R_{25}$, $R_{26}$, and $R_{27}$, stands for group selected from the group consisting of an alkyl group, an aralky group, and an aryl group, which may be substituted, wherein $R_{28}$ stands for an atom or a group selected from the group consisting of a hydrogen atom, a halogen atom, an alkyl group, and an alkoxy group, and wherein $R_{24}$ and $R_{25}$ may be bound together to form a ring, and $R_{24}$ or $R_{25}$ may be bound with $R_{28}$ to form a ring.

9. The electrophotographic photoreceptor as claimed in claim 3, wherein said change transport material is a distyryl compound represented by formula (VII):

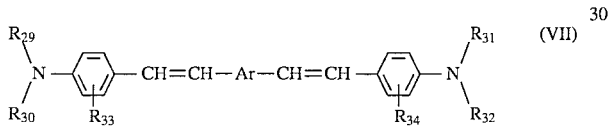

wherein each of $R_{29}$, $R_{30}$, $R_{31}$, and $R_{32}$ stands for a group selected from the group consisting of an alkyl group and an aryl group, which may be substituted wherein each of $R_{33}$ and $R_{34}$ stands for an atom or a group selected from the group consisting of a hydrogen atom, a halogen atom, an alkyl group, and an alkoxy group, and wherein Ar stands for an aryl group or an aromatic heterocyclic group.

10. The electrophotographic photoreceptor as claimed in claim 1, wherein said one compound is present in an amount ranging from 1 to 20 percent by weight of said photosensitive layer.

11. The electrophotographic photoreceptor as claimed in claim 4, wherein said change transport material is a hydrazone compound represented by formula (VI):

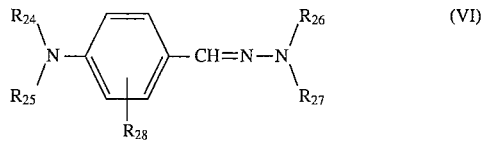

where each of $R_{24}$, $R_{25}$, $R_{26}$, and $R_{27}$ stands for a group selected from the group consisting of an alkyl group, an aralkyl group, and an aryl group, which may be substituted, wherein $R_{28}$ stands for an atom or a groups selected from the group consisting of a hydrogen atom, a halogen atom, an alkyl group, and an alkoxy group, and wherein $R_{24}$ and $R_{25}$ may be bound together to form a ring, and $R_{24}$ or $R_{25}$ may be bound with $R_{28}$ to form a ring.

12. The electrophotographic photoreceptor as claimed in claim 4, wherein said change transport material is distyryl compound represented by formula (VII):

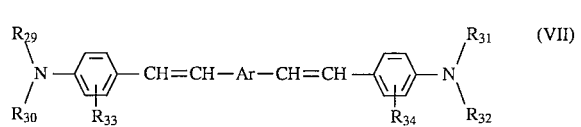

wherein each of $R_{29}$, $R_{30}$, $R_{31}$, and $R_{32}$ stand for a group selected from the group consisting of an alkyl group and an aryl group, which may be substituted, wherein each of $R_{33}$ and $R_{34}$ stands for an atom or a group selected from the group consisting of a hydrogen atom, a halogen atom, an alkyl group, and an alkoxy group, and wherein Ar stands for an aryl group or an aromatic heterocyclic group.

* * * * *